United States Patent
Chen et al.

(10) Patent No.: US 12,281,342 B2
(45) Date of Patent: Apr. 22, 2025

(54) EXTRACTION OF ANTIMETHANOGENIC COMPOUNDS

(71) Applicant: Synergraze Inc., Calgary (CA)

(72) Inventors: Jianwei Chen, Calgary (CA); Tamara Lee Loiselle, Calgary (CA)

(73) Assignee: Synergraze Inc., Calgary (CA)

( * ) Notice: Subject to any disclaimer, the term of this patent is extended or adjusted under 35 U.S.C. 154(b) by 0 days.

(21) Appl. No.: 18/891,931

(22) Filed: Sep. 20, 2024

(65) Prior Publication Data

US 2025/0066822 A1    Feb. 27, 2025

Related U.S. Application Data

(63) Continuation of application No. PCT/CA2024/051095, filed on Aug. 23, 2024.

(60) Provisional application No. 63/578,538, filed on Aug. 24, 2023.

(51) Int. Cl.
   *C12P 5/02*    (2006.01)
   *C12N 1/12*    (2006.01)
   *C12R 1/89*    (2006.01)

(52) U.S. Cl.
   CPC .................. *C12P 5/02* (2013.01); *C12N 1/12* (2013.01); *C12R 2001/89* (2021.05)

(58) Field of Classification Search
   CPC ....................................................... C12P 5/02
   See application file for complete search history.

(56) References Cited

U.S. PATENT DOCUMENTS

| | | | |
|---|---|---|---|
| 3,660,562 A | 5/1972 | Grass, Jr. et al. |
| 3,774,314 A | 11/1973 | Youngs |
| 4,251,506 A | 2/1981 | Laby |
| 4,649,143 A | 3/1987 | Kantor et al. |
| 11,439,604 B1 | 9/2022 | Serrano |
| 11,529,310 B2 | 12/2022 | Lay et al. |
| 12,116,608 B2 | 10/2024 | Chen |
| 2005/0142169 A1 | 6/2005 | Imafidon et al. |
| 2009/0258030 A1 | 10/2009 | Chi et al. |

(Continued)

FOREIGN PATENT DOCUMENTS

| | | |
|---|---|---|
| AU | 706697 B2 | 6/1999 |
| AU | 2021102541 A4 | 7/2021 |

(Continued)

OTHER PUBLICATIONS

Magnusson et al., "Using oil immersion to deliver a naturally-derived, stable bromoform product from the red seaweed *Asparagopsis taxiformis*," Algal Research 51(102065):1-7, 2020.*

(Continued)

*Primary Examiner* — Rosanne Kosson
(74) *Attorney, Agent, or Firm* — COOLEY LLP

(57) ABSTRACT

The present disclosure relates to liquid (e.g., water-soluble) compositions comprising antimethanogenic compounds, and methods of administering the same to reduce enteric methane emissions from ruminant animals, and/or improve feed-efficiency. Certain disclosed compositions exhibit improved rapid effect over prior art compositions. The disclosure further relates to methods of concentrating antimethanogenic compounds, extracting antimethanogenic compounds, and methods of increasing the bioavailability of antimethanogenic compounds.

20 Claims, 2 Drawing Sheets

(56) References Cited

U.S. PATENT DOCUMENTS

| | | |
|---|---|---|
| 2013/0196023 A1 | 8/2013 | Holma |
| 2016/0165928 A1 | 6/2016 | Hoffmann Pegoraro et al. |
| 2017/0273895 A1 | 9/2017 | Pompejus |
| 2018/0271922 A1 | 9/2018 | Machado et al. |
| 2018/0289816 A1 | 10/2018 | Pimentel et al. |
| 2019/0174793 A1 | 6/2019 | Tomkins et al. |
| 2019/0277833 A1 | 9/2019 | Gottlieb et al. |
| 2021/0315952 A1 | 10/2021 | Farmer et al. |
| 2022/0192229 A1 | 6/2022 | Duval et al. |
| 2024/0060092 A1 | 2/2024 | Chen et al. |

FOREIGN PATENT DOCUMENTS

| | | |
|---|---|---|
| EP | 0164241 A2 | 12/1985 |
| WO | WO-2020243792 A1 | 12/2020 |
| WO | WO-2021163148 A1 | 8/2021 |
| WO | WO-2021205420 A1 | 10/2021 |
| WO | WO-2022136857 A1 | 6/2022 |
| WO | WO-2023275152 A1 | 1/2023 |
| WO | WO-2023150832 A1 | 8/2023 |
| WO | WO-2023212121 A2 | 11/2023 |
| WO | WO-2024013721 A1 | 1/2024 |
| WO | WO-2024073575 A1 | 4/2024 |

OTHER PUBLICATIONS

Machado et al., "Identification of bioactives from the red seaweed *Asparagopsis taxiformis* that promote antimethanogenic activity in vitro," J Appl Phycol 28:3117-3126, 2016.*

Choi, C.B., et al.; "Effects of feeding ethanol on growth performances, carcass characteristics, and lipid metabolism of finishing Korean cattle (Hanwoo) steers," Asian-Australas J Anim Sci.; 32(3):366-374 (2019).

Google AI Overview PG Vapor Pressure search result for "Propylene glycol vapor pressure kPa," [retrieved online Nov. 27, 2024] Google.com, 4 pages (2024).

Google AI Overview Vapor Pressure search result for "10%, 20% ethanol vapor pressure kPa at 20," [retrieved online Nov. 27, 2024] Google.com, 3 pages (2024).

Invitation to Pay Additional Fees for International Application No. PCT/CA2024/051095, dated Oct. 21, 2024, 2 pages.

Machado, L., et al.; "In Vitro Response of Rumen Microbiota to the Antimethanogenic Red Macroalga *Asparagopsis taxiformis*," Microb Ecol.; 75(3):811-818 (2018).

Nunes, N., et al.; "Nutraceutical potential of Asparagopsis taxiformis (Delile) Trevisan extracts and assessment of a downstream purification strategy," Heliyon; 4(11)e00957; pp. 1-28 (2018).

Afrif, M. et al.; "Effect of supplementary sodium nitrate and sulphur on methane production and growth rates in sheep and goats fed forage-based diet low in true protein," J Anim Plant Sci.; 26(1):69-78 (2016).

Agolin Ruminant, Product information, Agolin SA (Dec. 2020) [retrieved online Oct. 17, 2024] URL: https://dleaashjn.preview.infomaniak.website/wp-content/uploads/2021/04/AGOLIN-RUMINANT.pdf, 2 pages.

Alemu, A.W., et al.; "3-Nitrooxypropanol supplementation of a forage diet decreased enteric methane emissions from beef cattle without affecting feed intake and apparent total-tract digestibility," J Anim Sci.; 101:skad001; pp. 1-17 (2013).

Alvarez-Hess, P.S., et al.; "Effects of a range of effective inclusion levels of Asparagopsis armata steeped in oil on enteric methane emissions of dairy cows," Animal Feed Science and Technology, 310:115932, 11 pages (2024).

Antaya, N.T., et al.; "Production, milk iodine, and nutrient utilization in Jersey cows supplemented with the brown seaweed *Ascophyllum nodosum* (kelp meal) during the grazing season," J Dairy Sci.; 102(9):8040-8058 (2019).

Appuhamy, J.A.D.R.N., et al.; "Anti-methanogenic effects of monensin in dairy and beef cattle: a meta-analysis," J Dairy Sci.; 96(8):5161-5173 (2013).

Asanuma, N., et al.; "Effect of the addition of fumarate on methane production by ruminal microorganisms in vitro," J Dairy Sci.; 82(4):780-777 (1999).

Ascensao, A.M.D.; "Effects of nitrate and additional effect of probiotic on methane emissions and dry matter intake in Nellore bulls," Master's Thesis, Universidade de Trás-os-Montes e Alto Douro, Departamento de Zootecnia, Vila Real, Portugal, 2010 [retrieved online: Oct. 16, 2024] URL: https://repositorio.utad.pt/server/api/core/bitstreams/0a9aeb4f-8e56-4a83-8b79-f7fba5b9f7aa/content; 76 pages.

Bayaru, E., et al; "Effect of Fumaric Acid on Methane Production, Rumen Fermentation and Digestibility of Cattle Fed Roughage Alone," Nihon Chikusan Gakkaiho; Anim. Sci. J.; 72(2):139-146 (2001).

Beauchemin, K.A., et al.; "Review: Fifty years of research on rumen methanogenesis: lessons learned and future challenges for mitigation," Animal; 14(S1):s2-s16 (2020).

Buchanan-Smith, J., et al.; "Optimizing Feedlot Feed Efficiency," Beef Cattle Research Council, 2019 [retrieved online Sep. 27, 2024] URL: https://www.beefresearch.ca/topics/optimizing-feedlot-efficiency/, 11 pages.

Cameron, M. R., et al.; "Growth and slaughter traits of Boer x Spanish, Boer x Angora, and Spanish goats consuming a concentrate-based diet," J Anim Sci. (Jun. 2001); 79(6):1423-1430.

Canadian Food Inspection Agency "Monensin (MOS)—Medicating ingredient brochure," Animal health, Livestock feeds, Compendium of Medicating Ingredient Brochures, Nov. 2022 [retrieved online Oct. 17, 2024] URL: https://inspection.canada.ca/en/animal-health/livestock-feeds/medicating-ingredients/monensin#a4, 14 pages.

Carter J.N. et al.; "Reactivity of recombinant and mutant vanadium bromoperoxidase from the red alga *Corallina officinalis*," J Inorg Biochem. (2002); 91(1):59-69.

Choudhury, P.K., et al.; "Reducing Enteric Methanogenesis through Alternate Hydrogen Sinks in the Rumen," Methane; 1(4):320-341 (2022).

Claffey, N.A., et al.; "Effect of forage to concentrate ratio and duration of feeding on growth and feed conversion efficiency of male lambs," Transl Anim Sci. (Jun. 2018); 2(4):419-427.

De Bhowmick, G., et al.; "Potential of Seaweeds to Mitigate Production of Greenhouse Gases during Production of Ruminant Proteins," Glob Chall.; 7(5):2200145, 18 pages (2023).

Demeyer, D., et al.; "Competitive inhibition of "in vitro" methane production by mixed rumen bacteria," Arch Int Physiol Biochim.; 75(1):157-159 (1967).

Ding, H., et al.; "Potential use of garlic products in ruminant feeding: A review," Anim Nutr.; 14:343-355 (2023).

Duin, E.C., et al.; "Mode of action uncovered for the specific reduction of methane emissions from ruminants by the small molecule 3-nitrooxypropanol," PNAS USA; 113(22):6172-6177 (2016).

Eason, C.T., et al.; "Methane reduction, health and regulatory considerations regarding Asparagopsis and bromoform for ruminants," New Zealand Journal of Agricultural Research, 31 pages (2023).

Fefac "Use of Bovaer® in dairy cows (methane emissions)," Regulation (EU) 2022/565; Jun. 2, 2023 [retrieved online Oct. 17, 2024] URL: https://fefac.eu/pages/sustainable-animal-feeding-strategies/ruminants/use-of-bovaer-in-dairy-cows-methane-emissions/; 2 pages.

George, M.M., et al.; "Effect of SeaFeed, a canola oil infused with Asparagopsis armata, on methane emissions, animal health, performance, and carcass characteristics of Angus feedlot cattle," Transl Anim Sci ; 8:txae116; pp. 1-11 (2024).

Hulshof, R.B.A., et al.; "Dietary nitrate supplementation reduces methane emission in beef cattle fed sugarcane-based diets," J Anim Sci.; 90(7):2317-2323 (2012), 8 pages.

International Search Report and Written Opinion for International Application No. PCT/IB2023/057246 dated Oct. 26, 2023, 10 pages.

Inthapanya, S.; "Effect of potassium nitrate and urea as fermentable nitrogen sources on growth performance and methane emissions in local "Yellow" cattle fed lime (Ca(OH)2) treated rice straw supplemented with fresh cassava foliage," Livestock Research for Rural

(56) References Cited

OTHER PUBLICATIONS

Development; 24(27); pp. 1-12 [retrieved online Oct. 17, 2024] URL: https://www.lrrd.org/lrrd24/2/sang24027.htm (2012).
Iwamoto, M., et al.; "Effects of nitrate combined with fumarate on methanogenesis, fermentation, and cellulose digestion by mixed ruminal microbes in vitro," Animal Science Journal; 70(6):471-478 (1999).
Janssen, P.H., et al.; "Structure of the archaeal community of the rumen," Appl Environ Microbiol.; 74(12):3619-3625 (2008).
Johnson, E.D., et al.; "Some effects of methane inhibition in ruminants (steers)," Can. J. Animal. Sci., (Dec. 1972), pp. 703-712.
Kebreab, E., et al.; "Strategies to reduce Methane emissions from enteric and lagoon sources," Contract 17RD018; University of California, Davis, One Shields Avenue, Davis, CA; prepared for State of California Air Resources Board Research Division; Jan. 8, 2021, 96 pages.
Kinley, R., et al.; "In Vitro Evaluation of the Antimethanogenic Potency and Effects on Fermentation of Individual and Combinations of Marine Macroalgae," Am. J. Plant Sci., (Oct. 2016), 7(14):2038-2054.
Kinley, R.D. et al.; "Mitigating the carbon footprint and improving productivity of ruminant livestock agriculture using a red seaweed," Journal of Cleaner Production (2020); 259:120836, 10 pages.
Kinley, R.D. et al.; "The red macroalgae *Asparagopsis taxiformis* is a potent natural antimethanogenic that reduces methane production during in vitro fermentation with rumen fluid," Animal Production Science (2016); 56(3):282-289.
Kolver, E.S., et al.; "Fumarate reduces methane production from pasture fermented in continuous culture," Proc. N. Z. Soc. Anim.; 64:155-159 (2004).
Lewis, S. J., et al., "Feedlot performance and carcass traits of Boer goat crosses and Spanish male kids [Abstract]," (1997) Journal of Animal Science, 75(Suppl. 1), p. 40 (2 pages).
Li, X. et al.; "Asparagopsis taxiformis decreases enteric methane production from sheep," Animal Production Science (2016), 58(4):681-688, 8 pages.
Li, X.Z., et al.; "Effects of dietary linseed oil and propionate precursors on ruminal microbial community, composition, and diversity in Yanbian yellow cattle," PLoS One (May 2015); 10(5):e0126473, 15 pages.
Liang, Y., et al.; "Effects of spirulina supplementation on lipid metabolism disorder, oxidative stress caused by high-energy dietary in Hu sheep," Meat Sci., (Jun. 2020); 164:108094, 9 pages.
Lin, C.Y. et al.; "Bromoform production from seawater treated with bromoperoxidase," Limnology and Oceanography (2012); 57(6):1857-1866.
Lopez, S., et al.; "Influence of sodium fumarate addition on rumen fermentation in vitro," Br J Nutr.; 81(1):59-64 (1999).
Magnusson, M., et al.; "Using oil immersion to deliver a naturally-derived, stable bromoform product from the red seaweed *Asparagopsis taxiformis*," Algal Research (2020); 51:102065, 7 pages.
McGinn, S.M., et al.; "Micrometeorological Methods for Measuring Methane Emission Reduction at Beef Cattle Feedlots: Evaluation of 3-Nitrooxypropanol Feed Additive," J Environ Qual.; 48(5):1454-1461 (2019).
Mtolera, M.S.P., et al.; "Stress-induced production of volatile halogenated organic compounds in Eucheuma denticulatum (Rhodophyta) caused by elevated pH and high light intensities," European Journal of Phycology (1996) 31(1):89-95, 8 pages.
Myers, E. W., et al., "Optimal alignments in linear space", Bioinformatics, Computer applications in the biosciences (1988); 4(1): 11-17.
Newbold, C.J., et al.; "Propionate precursors and other metabolic intermediates as possible alternative electron acceptors to methanogenesis in ruminal fermentation in vitro," Br J Nutr.; 94(1):27-35 (2005).
Newbold, C.J., et al.; "Propionate precursors as possible alternative electron acceptors to methane in ruminal fermentation," Greenhouse Gases and Animal Agriculture: Proceedings of the 1st International Conference on Greenhouse Gases and Animal Agriculture, Obihiro, Japan, Nov. 7-11, 2001; Elsevier Science B. V.; pp. 151-154 (Abstract Only) 2 pages (2002).
Nolan, J.V., et al.; "Effects of dietary nitrate on fermentation, methane production and digesta kinetics in sheep," Animal Production Science; 50(8):801-806 (2010).
O'Hara, E., et al.; "Comparative analysis of macroalgae supplementation on the rumen microbial community: Asparagopsis taxiformis inhibits major ruminal methanogenic, fibrolytic, and volatile fatty acid-producing microbes in vitro," Front Microbiol.; 14:1104667; pp. 1-16 (2023).
Ondongo, N.E., et al.; "Long-term effects of feeding monensin on milk fatty acid composition in lactating dairy cows" J Dairy Sci.; 90(11):5126-5133 (2007).
Patra, A.K., et al.; "Effects of Adaptation of In vitro Rumen Culture to Garlic Oil, Nitrate, and Saponin and Their Combinations on Methanogenesis, Fermentation, and Abundances and Diversity of Microbial Populations," Front Microbiol.; 6:1434; pp. 1-11 (2015).
Pitta, D.W., et al.; "Symposium review: Understanding diet-microbe interactions to enhance productivity of dairy cows," J Dairy Sci.; 101(8):7661-7679 (2018).
Poulsen, M., et al.; "Methylotrophic methanogenic Thermoplasmata implicated in reduced methane emissions from bovine rumen," Nat Commun.; 4:1428, 9 pages (2013).
Rogelj, J., et al.; "Mitigation Pathways Compatible with 1.5 in the Context of Sustainable Development," Global warming of 1.5 C, Intergovernmental Panel on Climate Change (2018); Chapter 2, pp. 93-174; [retrieved online Aug. 26, 2024] URL: https://www.ipcc.ch/site/assets/uploads/sites/2/2019/05/SR15_Chapter2_High_Res.pdf, 82 pages.
Romero, P., et al.; "Evaluating the effect of phenolic compounds as hydrogen acceptors when ruminal methanogenesis is inhibited in vitro—Part 2. Dairy goats," Animal; 17(5):100789; pp. 1-11 (2023).
Roque, B.M. et al.; "Inclusion of Asparagopsis armata in lactating dairy cows' diet reduces enteric methane emission by over 50 percent," Journal of Cleaner Production (2019); 234:132-138.
Sar, C., et al.; "Manipulation of rumen methanogenesis by the combination of nitrate with Beta1-4 galacto-oligosaccharides or nisin in sheep," Anim. Feed Sci. Technol.; 115(1-2):129-142 (2004).
Sea Forest "How SeaFeed ™ works to combat climate change," [retrieved online Oct. 17, 2024] URL: https://www.seaforest.com.au/how-asparagopsis-works; 4 pages (Publication Date Unknown).
Shike, D. W., "Beef cattle feed efficiency," [Conference session] (2013) Driftless Range Beef Conference, Dubuque, IA, United States. https://dr.lib.iastate.edu/entities/publication/dd175f9a-824e-4ac3-9b79-f56551ad8d13, 2 pages.
Shima, S., et al.; "Structure and function of enzymes involved in the methanogenic pathway utilizing carbon dioxide and molecular hydrogen," J. Biosci Bioeng.; 93(6):519-530 (2002).
Shimonishi, M. et al.; "Cloning and expression of the gene for a vanadium-dependent bromoperoxidase from a marine macro-alga, *Corallina pilulifera*," FEBS Lett., (1998); 428(1-2):105-110.
Sigma-Aldrich: Sodium formate, product specification; (2010), 1 page.
Silivong, P., et al.; "Effect of sulphur and calcium nitrate on methane production by goats fed a basal diet of molasses supplemented with Mimosa (*Mimosa pigra*) foliage," Livestock Research for Rural Development; vol. 23, Article #58 [retrieved online Oct. 17, 2024] URL: http://www.lrrd.org/lrrd23/3/sili23058.htm, 6 pages (2011).
Sophal, C., et al.: "Nitrate replacing urea as a fermentable N source decreases enteric methane production and increases the efficiency of feed utilization in Yellow cattle," Livestock Research for Rural Development; vol. 25, Article #113 [retrieved online Oct. 17, 2024] URL: http://www.lrrd.org/lrrd25/7/soph25113.htm, 6 pages (2013).
Stender, D.R., "Swine feed efficiency: Influence of market weight," [Fact sheet] (2012), Iowa State University, 2 pages, https://dr.lib.iastate.edu/handle/20.500.12876/4997.
Stiger-Poureau, V., et al.; "Macroalgal diversity for sustainable biotechnological development in French tropical overseas territories," Botanica Marina 63(1):17-41 (2020).
Thapa, H.R., et al.; "Genetic and Biochemical Reconstitution of Bromoform Biosynthesis in Asparagopsis Lends Insights into Seaweed Reactive Oxygen Species Enzymology," ACS Chemical Biology (2020), 15(6):1662-1670, Supplementary Information, 40 pages.

(56) References Cited

OTHER PUBLICATIONS

Thapa, H.R., et al.; "Genetic and Biochemical Reconstitution of Bromoform Biosynthesis in Asparagopsis Lends Insights into Seaweed Reactive Oxygen Species Enzymology," ACS Chemical Biology, Jun. 19, 2020, 15(6):1662-1670, 18 pages.

Tieves, F., et al.; "Formate Oxidase (FOx) from Aspergillus oryzae: One Catalyst Enables Diverse H2O2-Dependent Biocatalytic Oxidation Reactions," Angew Chem Int Ed Engl., (2019); 58(23):7873-7877.

Ungerfeld, E.M.; "Metabolic Hydrogen Flows in Rumen Fermentation: Principles and Possibilities of Interventions," Front Microbiol.; 11:589; pp. 1-21 (2020).

U.S. EPA: "SNEP: Agriculture and Aquaculture: Food for Thought," (Oct. 2020) [retrieved online Aug. 26, 2024] URL: https://www.epa.gov/sites/default/files/2021-03/documents/agriculture-aquaculture-food-thought.pdf, 5 pages.

U.S. Appl. No. 18/821,591, filed Aug. 30, 2024, by Inventors Jianwei Chen, et al.

U.S. Appl. No. 18/891,937, filed Sep. 20, 2024, by Inventor Jianwei Chen, et al.

Vadronova, M., et al.; "Combined effects of nitrate and medium-chain fatty acids on methane production, rumen fermentation, and rumen bacterial populations in vitro," Sci Rep; 13(1):21961; pp. 1-12 (2023).

Van Zijderveld, S.M., et al.; "Nitrate and sulfate: Effective alternative hydrogen sinks for mitigation of ruminal methane production in sheep," J. Dairy Sci.; 93(12):5856-5866 (2010).

Van Zijderveld, S.M., et al.; "Persistency of methane mitigation by dietary nitrate supplementation in dairy cows," J Dairy Sci ; 94(8):4028-4038 (2011).

Wang, Z., et al.; "Investigation and manipulation of metabolically active methanogen community composition during rumen development in black goats," Sci Rep.; 7(1):422, 14 pages (2017).

Wever, R. et al.; "Brominating activity of the seaweed *Ascophyllum nodosum*: Impact on the biosphere," Environ. Sci. Technol. (1991); 25(3):446-449.

Williams, S.R.O., et al.; "The effects of feeding liquid or pelleted formulations of Asparagopsis armata to lactating dairy cows on methane production, dry matter intake, milk production and milk composition," Animal Feed Science and Technology, 309:115891, 13 pages (2024).

Wood, J.M. et al.; "The reaction of multihalogenated hydrocarbons with free and bound reduced vitamin B 12," Biochemistry (May 1968); 7(5):1707-1713.

Wood, T.A., et al.; "Encapsulated fumaric acid as a feed ingredient to decrease ruminal methane emissions," Anim. Feed Sci. Technol.; 152(1-2):62-71 (2009).

Zesiger, C., et al., "Market Animal Feed Efficiency: A Tool for Evaluating Feed Conversion," Utah State University Extension (2022) Paper 2269. https://digitalcommons.usu.edu/extension_curall/2269, [retrieved online Nov. 21, 2023], 4 pages.

Zhou, Z., et al.; "Effects of methanogenic inhibitors on methane production and abundances of methanogens and cellulolytic bacteria in in vitro ruminal cultures," Appl Environ Microbiol.; 77(8):2634-2639 (2011).

International Search Report and Written Opinion for PCT Application No. PCT/CA2024/051095 mailed Dec. 10, 2024, 18 pages.

\* cited by examiner

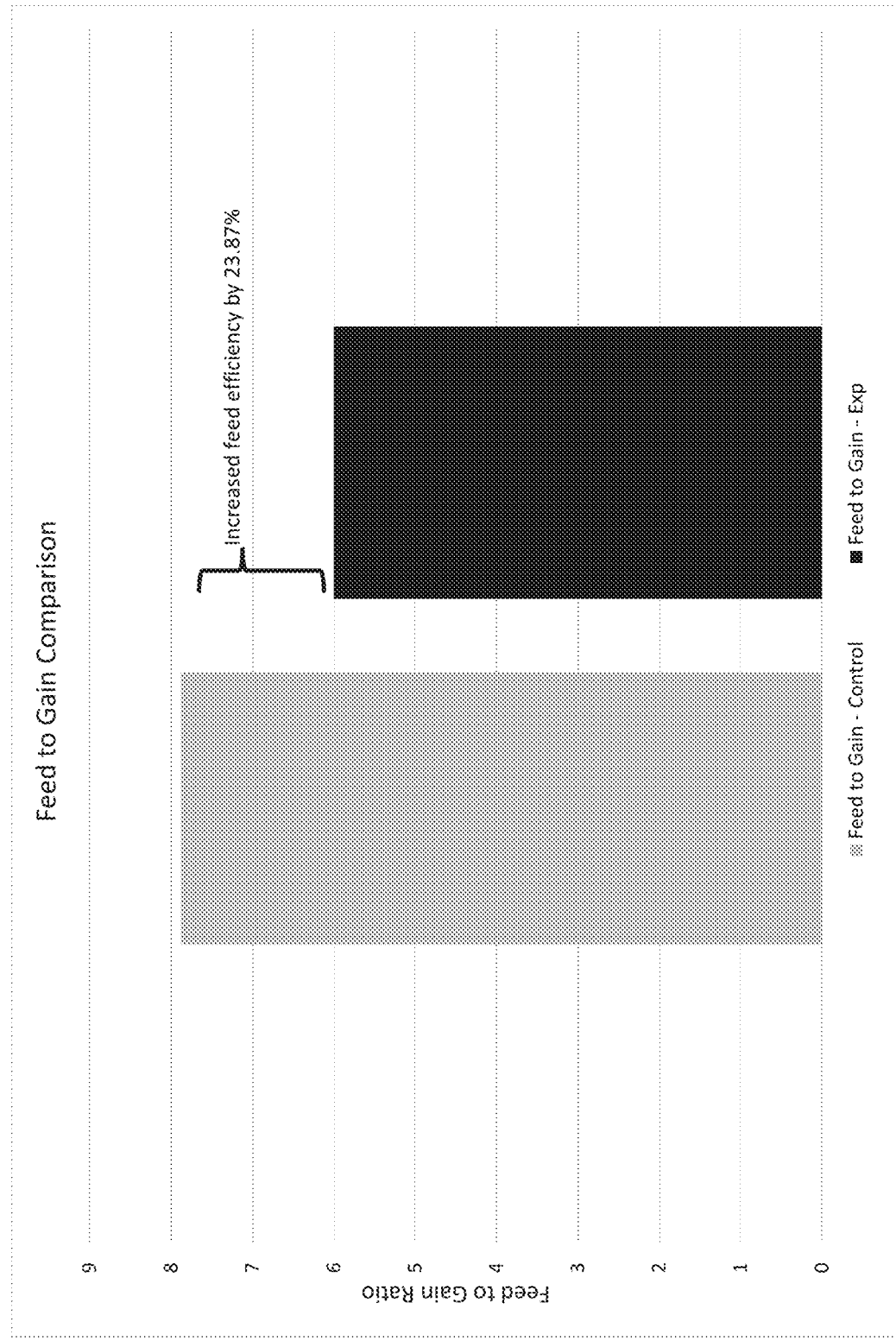

EXTRACTION OF ANTIMETHANOGENIC COMPOUNDS

CROSS-REFERENCE TO RELATED APPLICATION

This application is a continuation of International Application No. PCT/CA2024/051095, filed on Aug. 23, 2024, which claims the benefit of priority to U.S. Provisional Application No. 63/578,538, filed on Aug. 24, 2023, the entire contents of which are incorporated herein by reference.

FIELD

The present disclosure relates to water-soluble compositions comprising antimethanogenic compounds and methods of using the same to increase feed efficiency and reduce enteric methane emissions from ruminant animals. The disclosure further relates to methods of extracting and concentrating antimethanogenic compounds.

BACKGROUND

Ruminant animals produce and expel methane as part of their digestive process, specifically during the fermentation of undigested food in the rumen. However, methane is a greenhouse gas that is contributing to global warming. In terms of its potency, methane is 34-times more powerful than $CO_2$ on a 100-year timescale and 86-times more powerful over a 20-year timescale for altering earth's climate. By some estimates, methane emissions from agricultural production need to be reduced by 24-47% by 2050 relative to 2010 to meet the 1.5° C. target of the Paris Agreement (Rogelj J., et al., *Global Warming of 1.5° C.* Intergovernmental Panel on Climate Change; Geneva, Switzerland: 2018. Mitigation pathways compatible with 1.5° C. in the context of sustainable development; pp. 93-174).

37% of methane emissions from human activity are the direct result of our livestock and agricultural practices. A single cow can produce between 154 and 264 pounds of methane gas per year; combined, methane emissions from cattle raised specifically for meat production emit at least 231 billion pounds of methane into the atmosphere each year (Agriculture and Aquaculture: Food for Thought, October 2020, available on the world wide web at epa.gov/snep/agriculture-and-aquaculture-food-thought).

Both microalgae and macroalgae are known to produce metabolites (for example halogenated compounds) that inhibit enteric methane production (antimethanogenic compounds). An example of one such metabolite is bromoform ($CHBR_3$). Bromoform is a halogenated methane that is naturally produced by many types of algae, such as those belonging to the genus *Asparagopsis*. Algae that are known to naturally produce bromoform have an enzyme (bromoperoxidase) that catalyzes the formation of bromoform.

Bromoform is known to be an inhibitor of methanogenesis in ruminant animals, and studies have been conducted on reducing methane production in ruminant animals by including trace amounts of bromoform with their feed. Specifically, halogenated aliphatic compounds with 1 or 2 carbons such as bromoform block the function of corrinoid enzymes and inhibit cobamide-dependent methyl group transfer in methanogenesis (Wood J. et al., Reaction of multihalogenated volatile fatty acids with free and bound reduced vitamin B12, *Biochem.* 7 (1968) pp. 1707-13. See also Roque B. M. et al., Inclusion of *Asparagopsis armata* in lactating dairy cows' diet reduces enteric methane emission by over 50 percent, *J. Clean. Prod.*, 234 (2019) pp. 132-138; Kinley R. D. et al., The red macroalgae *Asparagopsis taxiformis* is a potent natural antimethanogenic that reduces methane production during in vitro fermentation with rumen fluid, *Anim. Prod. Sci.*, 56 (2016), pp. 282-289; Li X. et al., *Asparagopsis taxiformis* decreases enteric methane production from sheep, *Anim. Prod. Sci.*, 58 (2018), pp. 681-688; and Kinley R. D. et al., Mitigating the carbon footprint and improving productivity of ruminant livestock agriculture using a red seaweed, *J. of Cleaner Prod.* 259 (2020).

Currently, one conventional way of including antimethanogenic compounds in animal feed is to collect and freeze-dry algae that are known to naturally produce these compounds (such as those of the genus *Asparagopsis*) and to introduce the freeze-dried algae into the feed. However, algae such as *Asparagopsis* spp. may contain malodorous components. These odor triggering components reduce the palatability of the feed that has been supplemented with compositions derived from algal biomass. Additionally, freeze-drying algae is not cost-effective, and the product has a relatively short shelf-life.

Antimethanogenic compounds in edible oil is another approach, and has several advantages over freeze-dried algae. One such advantage is that the oil can stabilize the antimethanogenic compound, thereby increasing the shelf life of the product. Another is that it removes the malodorous components that make freeze-dried algae less palatable. However, the oil must be administered via an animal feed product, something that's not realistic for free-range cattle.

Thus, there is a need for more efficient compositions and methods for delivering antimethanogenic compounds to ruminant animals.

SUMMARY OF THE DISCLOSURE

In some aspects, the disclosure relates to a water-soluble composition including: a) an antimethanogenic compound; and b) a carrier, wherein the carrier is miscible and/or soluble with water, and wherein the antimethanogenic compound is miscible and/or soluble with the carrier.

In some aspects, the disclosure relates to a water-soluble composition including: a) an antimethanogenic compound selected from the group consisting of methyl bromide, methyl chloride, methyl iodide, methyl fluoride, bromodichloromethane, trichlorethylene, bromoform, chloroform, iodoform, fluoroform, dibromomethane, and a combination thereof; and b) a carrier selected from Table 2, wherein the antimethanogenic compound is dissolved in the carrier, and wherein the carrier is miscible and/or soluble with water.

In some aspects, the disclosure relates to an animal feed composition including: a) an antimethanogenic compound dissolved in a carrier that is miscible and/or soluble in water; and b) an animal nutritional component; wherein the animal feed composition reduces enteric methane emissions and/or increases feed efficiency when ingested by a ruminant animal.

In some aspects, the disclosure relates to a composition including: a) an algae extract; and b) a carrier, wherein the algae extract includes an anti-methanogenic compound, and wherein the carrier is miscible and/or soluble with water.

In some aspects, the disclosure relates to a composition including: bromoform dissolved in propylene glycol, wherein the composition includes at least 0.1 mg of bromoform per gram of propylene glycol.

In some aspects, the disclosure teaches a method of capturing antimethanogenic compounds, including the steps of: a) providing a first solution including an antimethanogenic compound in a non-water-soluble carrier; b) providing a second solution including a water-soluble carrier selected from Table 2; and c) contacting the first solution and second solution, thereby transferring the antimethanogenic compound from the first solution to the second solution.

In some aspects, the disclosure teaches a method of capturing antimethanogenic compounds, including the steps of: a) providing a first solution including an antimethanogenic compound in an oil carrier; b) providing a second solution including a propylene glycol; and c) contacting the first solution and second solution, thereby transferring the antimethanogenic compound from the first solution to the second solution.

In some aspects, the disclosure teaches a method of capturing antimethanogenic compounds, including the steps of: a) capturing antimethanogenic compounds from a water solution by contacting the water solution with a non-miscible oil, thereby transferring antimethanogenic compounds to the non-miscible oil; b) separating the non-miscible oil from the water, thereby making a first solution; and c) contacting the first solution with a second solution including a water-soluble carrier selected from Table 2, thereby transferring the antimethanogenic compound from the first solution to the second solution.

In some aspects, the disclosure teaches a method of capturing antimethanogenic compounds, including the steps of: a) providing a first solution including an antimethanogenic compound in an oil carrier; b) providing a second solution including a water-soluble carrier; and c) contacting the first solution and second solution, thereby transferring the antimethanogenic compound from the first solution to the second solution.

In some aspects, the disclosure teaches a method of capturing antimethanogenic gas, including the steps of: contacting the antimethanogenic gas with a water-soluble carrier selected from Table 2; wherein at least 10%, 20%, 30%, 40%, 50%, 60%, 70%, 80%, or 90% of the antimethanogenic gas is retained within the water-soluble carrier.

In some aspects, the disclosure teaches a method of capturing antimethanogenic gas, including the steps of: contacting the antimethanogenic gas with an oil carrier; wherein at least 10%, 20%, 30%, 40%, 50%, 60%, 70%, 80%, or 90% of the antimethanogenic gas is retained within the oil carrier.

In some aspects, the disclosure teaches a method of concentrating antimethanogenic compounds, including the steps of: contacting the antimethanogenic compound with a water-soluble carrier selected from Table 2 or an oil; wherein the antimethanogenic compound reaches a concentration of at least 10, 20, 30, 40, 50, or 60 grams of antimethanogenic compound per milliliter of water-soluble carrier or oil.

In some aspects, the disclosure teaches a method of extracting antimethanogenic compounds from a cell, including the steps of: a) providing a cell containing an antimethanogenic compound; b) heating the cell, thereby creating a heated gas above the cell, said heated gas including the antimethanogenic compound; and c) contacting the heated gas with a liquid carrier; wherein at least 10%, 20%, 30%, 40%, 50%, 60%, 70%, 80%, or 90% of the antimethanogenic compound in the heated gas is retained within the liquid carrier.

In some aspects, the disclosure teaches a method of extracting antimethanogenic compounds from a cell, including the steps of: a) providing a cell containing an antimethanogenic compound; b) off gassing the cell, thereby creating a gas above the cell, said gas including the antimethanogenic compound; and c) contacting the gas of step (b) with a liquid carrier; wherein at least 10%, 20%, 30%, 40%, 50%, 60%, 70%, 80%, or 90% of the antimethanogenic compound in the gas is retained within the liquid carrier.

The foregoing was intended as a summary only and of only some of the aspects of the disclosure. It was not intended to define the limits or requirements of the disclosure. Other aspects of the disclosure will be appreciated by reference to the detailed description of the embodiments.

BRIEF DESCRIPTION OF THE DRAWINGS

FIG. 2 is a bar graph showing the feed to gain ratio in control cattle versus cattle supplemented with a water-soluble composition of the present disclosure.

DEFINITIONS

Figure 1:
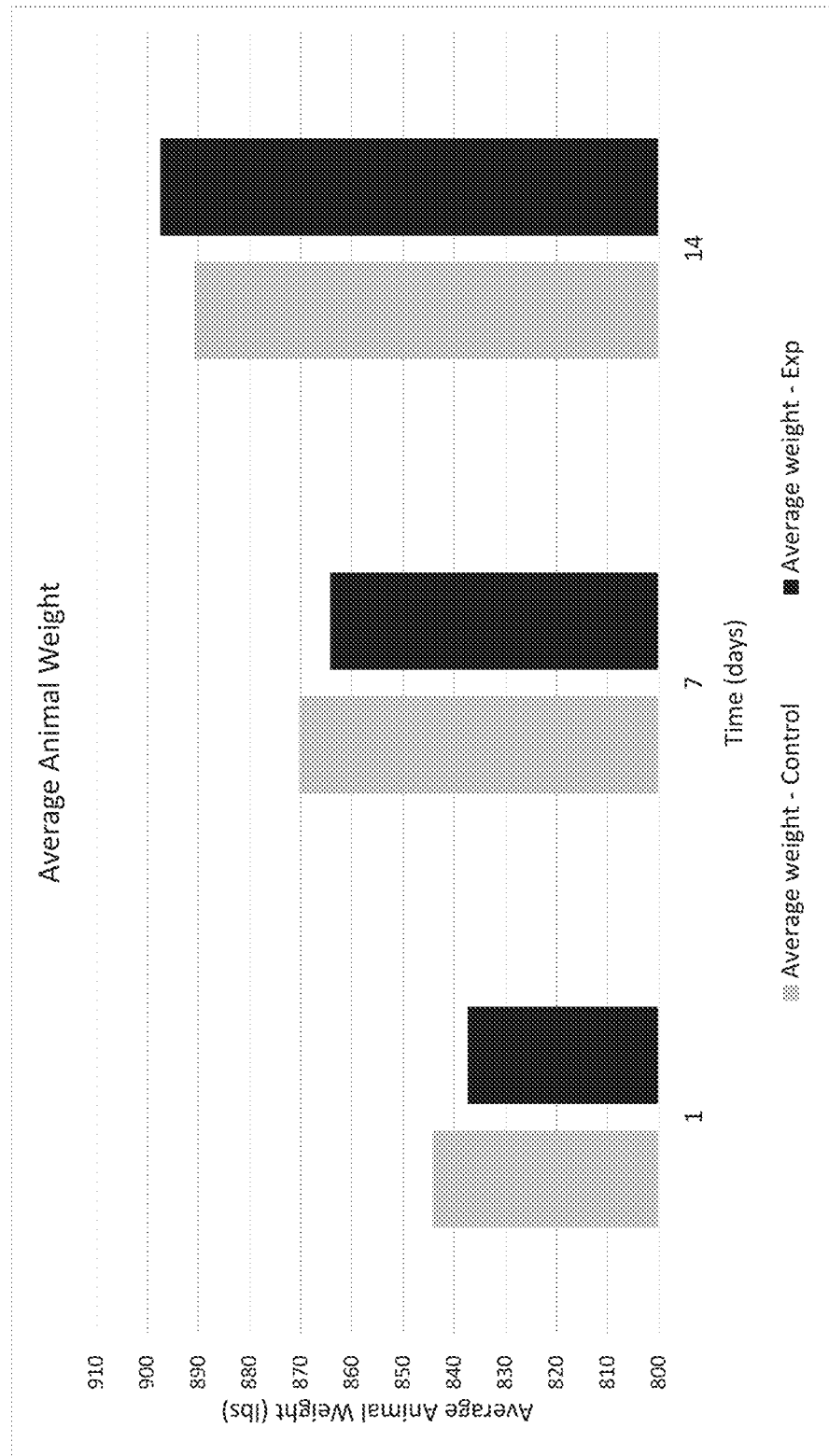
FIG. 1 is a bar graph showing the average animal weight in pounds over the course of two weeks in cattle supplemented with a water-soluble composition of the present disclosure compared to un-supplemented cattle.

In the description and tables which follow, a number of terms are used. In order to provide a clear and consistent understanding of the specification and claims, including the scope to be given such terms, the following definitions are provided.

The term "a" or "an" refers to one or more of that entity; for example, "a primer" refers to one or more primers or at least one primer. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

The term "about" when immediately preceding a numerical value means a range (e.g., plus or minus 10% of that value). For example, "about 50" can mean 45 to 55, "about 25,000" can mean 22,500 to 27,500, etc., unless such an interpretation would result in a value above or below range of possible values, such as below 0% or above 100% of a possible value. Furthermore, the phrases "less than about" a value or "greater than about" a value should be understood in view of the definition of the term "about" provided herein, as applied to any recited endpoint. Similarly, the term "about" when preceding a series of numerical values or a range of values (e.g., "about 10, 20, 30" or "about 10-30") refers, respectively to all values in the series, or the endpoints of the range. Unless otherwise indicated, it is to be understood that all numbers expressing quantities, ratios, and numerical properties of ingredients, reaction conditions, and so forth, used in the specification and claims are contemplated to be able to be modified in all instances by the term "about".

The term "approximately" when immediately preceding a numerical value means a range (e.g., plus or minus 5% of that value). For example, "approximately 50" can mean 47.5 to 52.5, "approximately 25,000" can mean 23,750 to 26,250, etc., unless such an interpretation would result in a value above or below range of possible values, such as below 0% or above 100% of a possible value.

The term "including all ranges and subranges there between" or equivalents, are used herein to denote the intention that disclosure of any range or series of possible values, inherently also discloses all ranges and subranges encompassed by the highest and lowest values disclosed. This term includes the entire range from highest to lowest disclosed values, as well as subranges from any two or more disclosed points. This term is also intended to disclose any subranges encompassed anywhere within the highest and lowest disclosed values, including between two points that are explicitly recited in the document, up to one decimal point. Thus, disclosure of values 0, 5, 10, 15, 20, including all ranges and subranges therebetween, should be interpreted as also encompassing a range from 0-20, a range from 0-5 or 5-15, as well as a range from 2-16, or 3.1 to 19.8, etc.

Unless otherwise indicated, it is to be understood that all numbers expressing quantities, ratios, and numerical properties of ingredients, reaction conditions, and so forth, used in the specification are contemplated to be able to be modified in all instances by the term "including all ranges and subranges therebetween."

The term "antimethanogenic compound" or "anti-methanogenic compound" refers to any compound that inhibits methanogenesis in a ruminant.

The terms "bioactives" and "metabolites" may be used interchangeably to refer to compounds formed through the metabolic activity of algae.

"Bioproduct" as used herein refers to any product produced from or derived from a renewable biological resource.

As used herein, "enzymatic inhibitors" refer to compounds that inhibit the enzymatic activities needed in methanogenesis.

As used herein, "feed efficiency" refers to the feed to gain ratio (F:G), or feed conversion ratio (FCR), and is a measure of an animal's efficiency in converting feed nutrients into increased body mass. Feed is measured by pounds of dry matter. Thus, a F:G of 5:1 (or "5") would mean that for every five pounds of feed, the animal gained one pound of weight.

As used herein, "fresh algae" refers to algae that is alive and has never been frozen.

As used herein, "full spectrum" refers to a composition that retains the complex profile of naturally occurring compounds formed through metabolic activity by algae. For example, in some embodiments, a full spectrum composition from an algal biomass includes the antimethanogenic compound and vitamin B12 produced by the algae.

As used herein, "hydrogen receptors" are compounds that compete with methanogens in the rumen for the utilization of metabolic hydrogen.

The terms "microorganism" and "microbe" mean any microscopic unicellular organism and can include bacteria, microalgae, yeast, or fungi.

As used herein, "microflora modifying inhibitors" (MMIs) are compounds that inhibit gram-positive bacteria and protozoa, thereby decreasing the substrates for methanogenesis.

As used herein, "recombinant" refers to DNA, proteins, cells, or organisms that are man-made by combining genetic material from two different sources. As used herein the term "sequence identity" refers to the extent to which two optimally aligned polynucleotides or polypeptide sequences are invariant throughout a window of alignment of residues, e.g. nucleotides or amino acids. An "identity fraction" for aligned segments of a test sequence and a reference sequence is the number of identical residues which are shared by the two aligned sequences divided by the total number of residues in the reference sequence segment, i.e. the entire reference sequence or a smaller defined part of the reference sequence. "Percent identity" is the identity fraction times 100. Comparison of sequences to determine percent identity can be accomplished by a number of well-known methods, including for example by using mathematical algorithms, such as, for example, those in the BLAST suite of sequence analysis programs. Unless noted otherwise, the term "sequence identity" in the claims refers to sequence identity as calculated by Clustal Omega® using default parameters as of the filing date.

"W/W" or "w/w", in reference to proportions by weight, refers to the ratio of the weight of one substance in a composition to the weight of the composition.

As used herein, "and/or" refers to and encompasses any and all possible combinations of one or more of the associated listed items.

Portions of this disclosure relate to rapid release dosages for fast absorption/effects. As used herein the term "rapid absorption or rapid effect" refers to a composition which can make its entire active ingredient payload bioavailable within a pre-set dosage period of 4, 8, or 12 hours. Bioavailability of an active ingredient payload can be inferred based on the active ingredient effect taking place pre-set period (e.g., reduction in methane).

Overview

The present disclosure relates to water-soluble compositions comprising antimethanogenic compounds, and methods of administering the same to ruminant animals to reduce enteric methane emissions and improve feed-efficiency. The disclosure further relates to methods of concentrating antimethanogenic compounds, extracting antimethanogenic compounds, and methods of increasing the bioavailability of antimethanogenic compounds.

Antimethanogenic Compounds

Inhibitors of methanogenesis can be classified into three different types based on their mode of action. Those that act on the microflora itself are called microflora modifying inhibitors (MMIs). Those that serve as an alternative hydrogen sink in the rumen, and thus compete with the methanogens for hydrogen, are called hydrogen receptors (HRs). Those that interfere with or inhibit the enzymatic activities needed for methanogenesis are called enzymatic inhibitors (EIs). Persons having skill in the art will be familiar with inhibitors within each of these categories, which are described in more detail, below.

Microflora Modifying Inhibitors (MMIs)

Methanogens make up about 5% of the rumen microbiome, the rest being comprised of bacteria. *Methanobrevibacter* spp., *Candidatus methanomethylophilus*, *Methanosphaera* spp., and *Methanomicrobium* spp. are among the most abundant, but other species have been identified. For example, *Methanobacterium formicicum*, *Methanobacterium bryantii*, *Methanobrevibacter ruminantium*, *Methanobrevibacter millerae*, *Methanobrevibacter olleyae*, *Methanomicrobium mobile*, *Methanoculleus olentangyi*, and *Methanosarcina barkeri* (Janssen P. H. & Kirs M. Structure of the archaeal community of the rumen. *Appl. Environ. Microbiol.* 2008; 74: 3619-3625; Wang Z. et al., Investigation and manipulation of metabolically active methanogen community composition during rumen development in black goats. *Sci. Rep.* 2017; 7: 422). A group distantly related to the Thermoplasmatales has also been identified (Poulsen M. et al., Methylotrophic methanogenic Thermoplasmata implicated in reduced methane emissions from bovine rumen. *Nat. Commun.* 2013; 4: 1428). Example MMIs include, but are not limited to, monensin, nitroimidazoles, saponins, tannins, and combinations thereof.

Additional examples of MMIs include, for example nitroimidazoles such as metronidazole, metronidazole esters and/ or isomers or hydrophobic imidazole derivatives or rifaximin or neomycin sufficient to eradicate, substantially reduce, or reduce the enteric methanogen colonization. Additional examples of antibiotics include but are not limited to aminoglycosides (e.g., amikacin, gentamicin, kanamycin, neomycin, netilmicin, streptomycin, tobramycin, paromomycin), ansamycins (e.g., geldanamycin, herbimycin), carbacephems (e.g., loracarbef), carbapenems (e.g., ertapenem, doripenem, imipenem, cilastatin, meropenem), cephalosporins (e.g., first generation: cefadroxil, cefazolin, cefalotin or cefalothin, cefalexin; second generation: cefaclor, cefamandole, cefoxitin, cefprozil, cefuroxime; third generation: cefixime, cefdinir, cefditoren, cefoperazone, cefotaxime, cefpodoxime, ceftazidime, ceftibuten, ceftizoxime, ceftriaxone; fourth generation: cefepime; fifth generation: ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin), antibiotic polypeptides (e.g., bacitracin, colistin, polymyxin b), quinolones (e.g., ciprofloxacin, enoxacin, gatifloxacin, levofloxacin, lomefloxacin, moxifloxacin, norfloxacin, ofloxacin, trovafloxacin), rifamycins (e.g., rifampicin or rifampin, rifabutin, rifapentine, rifaximin), sulfonamides (e.g., mafenide, prontosil, sulfacetamide, sulfamethizole, sulfanilamide, sulfasalazine, sulfisoxazole, trimethoprim, trimethoprim-sulfamethoxazole (co-trimoxazole, "tmp-smx"), and tetracyclines (e.g., demeclocycline, doxycycline, minocycline, oxytetracycline, tetracycline) as well as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin combination, tinidazole, and combinations thereof.

Hydrogen Receptors (HRs)

A byproduct of the high starch diets broken down by rumen microbes is hydrogen production. If left unchecked, accumulated hydrogen has detrimental effects on the rumen, such as decreased pH, the deactivation of biomass-degrading enzymes, and a reduction in feed conversion. Methanogens in the rumen take hydrogen and combine it with $CO_2$ to produce $CH_4$, thus removing hydrogen from the rumen system. However, as discussed herein, methane is a greenhouse gas. Thus, one of the mechanisms to reduce enteric methane emissions is to provide an alternative hydrogen sink.

Examples of HRs include, but are not limited to, phenol, catechol, resorcinol, hydroquinone, pyrogallol, phloroglucinol, gallic acid, formic acid, sulfur (including for example sulfate, sodium sulfate), nitrate (including for example potassium nitrate, calcium ammonium nitrate, sodium nitrate, calcium nitrate), fumarate (including for example fumaric acid, sodium fumarate, sodium acrylate), and combinations thereof.

Enzymatic Inhibitors (EIs)

There are at least three anaerobic pathways archaea use to generate methane. The hydrogenotrophic pathway, where $CO_2$ and hydrogen are used and utilizes at least ten methanogen specific enzymes (Shima S, et al., 2002. Structure and function of enzymes involved in the methanogenic pathway utilizing carbon dioxide and molecular hydrogen. *J. Biosci. Bioeng.* 93:519-530). The methylotrophic pathway, where methanol and methylamines are used as substrates, and the aceticlastic pathway, where acetate is used to make methane. Antimethanogenic compounds classified as enzymatic inhibitors inhibit or interfere with one or more of the enzymes required for any one of these pathways.

Examples of EIs include, but are not limited to, 3-nitroxy propanol (3-NOP), which is an analog of methyl-coenzyme M and it inhibits methyl-coenzyme M reductase (Duin E. C. et al., Mode of action uncovered for the specific reduction of methane emissions from ruminants by the small molecule 3-nitrooxypropanol. *Proc. Natl. Acad. Sci. USA.* 2016; 113: 6172-6177), Agolin, Biochar, cinnamon, garlic (Ding H, Ao C, Zhang X. Potential use of garlic products in ruminant feeding: A review. *Anim Nutr.* 2023 Jul. 13; 14:343-355), allicin, Enterix™, oregano extract, and volatile halogenated organic compounds (VHOCs).

VHOCs are another type of EI that can be used as antimethanogenic compounds to inhibit microbial methanogenesis (R. D. Kinley et al. Mitigating the carbon footprint and improving productivity of ruminant livestock agriculture using a red seaweed J. Clean. Prod., 259 (2020)). Antimethanogenic compounds can also reduce acetate levels and or the acetate:propionate ratio, thereby reducing methanogenesis (R. Kinley et al. In vitro evaluation of the antimethanogenic potency and effects on fermentation of individual and combinations of marine macroalgae Am. J. Plant Sci., 07 (2016), pp. 2038-2054 and E. D. Johnson et al. Some effects of methane inhibition in ruminants (steers) Can. J. Animal. Sci., 52 (1972), pp. 703-712).

Macroalgae, such as seaweed, and microalgae produce a wide range of secondary metabolites that can be used for any number of purposes. Among these are VHOCs.

These algae produce various peroxidases, which react with hydrogen peroxide and organic matter to form VHOCs. As an example, in species of *Asparagopsis*, a peroxidase catalyzes the conversion of halide anions (i.e. Br–) to hypohalous acid (i.e. HOBr) with hydrogen peroxide acting as the oxidizing agent.

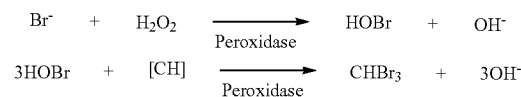

The resulting hypohalous acid (e.g. HOBr) is not stable and will react with selective substrates to form, for example, bromoform and other brominated compounds, such as dibromochloromethane (shown below). As discussed in more detail in later sections of this document, corresponding structures also form when other halides are used in the reaction.

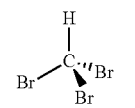

Bromoform
$\Delta H_{c\text{-}Br}$ 278 kj/mol

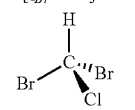

Dibromochloromethane (DBCM)

Examples of VHOCs include, but are not limited to, methyl halides-$CH_3Br$, $CH_3Cl$, $CH_3I$, $CH_3F$, bromodichloromethane ($CHBrCl_2$), trichlorethylene ($C2HCl_3$), bromoform ($CHBr_3$), chloroform ($CHCl_3$), iodoform ($CHI_3$), fluoroform ($CHF_3$), and dibromomethane ($CH_2Br_2$).

Bromoform ($CHBr_3$)

Bromoform is colorless to pale yellow, with a sweet odor. It is denser than water, and soluble in water though not at high concentrations. Bromoform is the most abundant VHOC produced by seaweeds of the genus *Asparagopsis*, but it is also produced by, for example, other red seaweeds (e.g. *Chondrus crispus, Gigartina stellata*), brown seaweeds (e.g. *Ascophyllum nodosum, Fucus vesiculosis Macrocystis pyrifera*) green seaweeds (e.g. *Enteromorpha linza, Ulva lacta*), blue green algae, microalgae, and phytoplankton.

Chloroform ($CHCl_3$)

Chloroform is a clear, colourless, volatile, non-flammable liquid with a pleasant, sweet odour. Chloroform can be produced during the atmospheric photodegradation of trichloroethylenes. It is produced by the tropical red algae (*Asparagopsis armata*) and by the red seaweed (*A. taxiformis*). Chloroform has been reported to be produced by micro algae in the North Sea and open ocean of the northeast Atlantic. Chloroform does not contain chromophores that absorb at wavelengths >290 nm and, therefore, is not expected to be susceptible to direct photolysis by sunlight. If released to soil, chloroform is expected to have very high to moderate mobility based upon Koc values of 34-196. Under normal environmental conditions, chloroform is not expected to undergo biodegradation in soil. However, chloroform may be anaerobically degraded by methanogenic bacteria in the presence of a primary substrate such as acetic acid.

Iodoform

Iodoform is a pale yellow, crystalline, volatile substance, with a penetrating and distinctive odor and sweetish taste. Iodoform may be synthesized in the haloform reaction by the reaction of iodine and sodium hydroxide with one of organic compounds selected from a methyl ketone ($CH_3COR$, where R is an organic side chain), acetaldehyde, ethanol, and secondary alcohols ($CH_3CHROH$, where R is an alkyl or aryl group).

Sources of Antimethanogenic Compounds for Use with the Disclosed Compositions and Methods Antimethanogenic compounds may be obtained from any number of sources, such as algae, fungi, yeast, and microorganisms. They may also be manufactured (synthetic).

Antimethanogenic Compounds Obtained from Algae

Many algal species are capable of producing commercially valuable bioactives, metabolites including antimethanogenic compounds, and can be induced to do so at commercially relevant levels (see for example U.S. patent application Ser. No. 18/496,409 (US 2024-0060092), which is hereby incorporated by reference in its entirety for all purposes).

In some embodiments of the disclosure, the antimethanogenic compound(s) is obtained from an algae of the genus *Asparagopsis*, for example, *A. armata, A. taxiformis, A. svedelli, A. delilei, A. hamifera, A. sanfordiana*. However, it is understood that other species of macroalgae and microalgae also produce antimethanogenic compounds. For example, other types of red algae, including, but not limited to, those of the Order Rhodophyta, Class Florideophyceae, including *Gracilaria* and *Plocamium*. In still a further embodiment, the red algae is of the genus *Gracilariales* or *Palmeria*. In another embodiment, the red algae is of the order Gigartinales or *Chondrus*.

In addition, the antimethanogenic compound(s) may be produced by brown algae. For example, those of class Phaeophyceae, such as the order Laminariales, including *Laminaria* spp., *Macrocystis pyrifera, Nereocystis* spp. and other kelps, as well as *Dictyota*.

Furthermore, the antimethanogenic compound(s) may be obtained from single or multiple species of algae and may comprise microalgae, macroalgae, or a combination of both.

Additional sources of antimethanogenic compounds include, for example, species of *Bonnemaisonia, Delisea, Ptilonia, Leptophyllis*, and/or *Pleuroblepharidella*.

In some embodiments, the antimethanogenic compound(s) is obtained from *Laminaria saccharina, Laminaria digitata, Fucus vesiculosis, Fuscus distichus, Alaria esculenta, Chorda filum, Ceramium rubrum, Corallina pilulifera, Pelvetia canaliculate, Ascophyllum nodusum, Chondrus crispus, Plocamium hamatum, Gigartina stellata, Enteromorpha linza, Ulva lacta, Bonnemaisonia hamifera, Asparagopsis taxiformis, Asparagopsis Armata, Gracilaria* spp., *Antithamnionella sarniensis, Antithamnion plumula*, or *Macrocystis pyrifera*.

In some embodiments, the antimethanogenic compound(s) is obtained from phytoplankton, such as a diatom species from *Nitzschia* and/or *Porosira*. In some embodiments, the antimethanogenic compound(s) is obtained from a species of green algae. In some embodiments, the antimethanogenic compound(s) is obtained from a species of blue green algae (also known as cyanobacteria), such as *Arthrospira platensis* or a species of *Chlorella*, including but not limited to, *Chlorella protothecoides*, and *Chlorella vulgaris*.

Antimethanogenic Compounds Obtained from Fungi

In some embodiments, the antimethanogenic compound(s) is obtained from a fungus. In some embodiments, the fungus is a *Pleurotus* spp. fungi, e.g., *P. ostreatus* (oyster mushrooms), a *Lentinula* spp. fungi, e.g., *L. edodes* (shiitake mushrooms), and/or a *Trichoderma* spp. fungi, e.g., *T. harzianum* and/or *T. viride*. More description of non-limiting examples of fungi can be found, for example, in US 2021/0315952 and WO 2021/163148, the content of each of which is incorporated by reference in its entirety for all purposes.

Antimethanogenic Compounds Obtained from Yeast

In some embodiments, the antimethanogenic compound(s) is obtained from a yeast. In some embodiments, the yeast is Wickerhamomyces *anomalus, Saccharomyces* spp. (e.g., *S. cerevisiae* and/or *S. boulardii*), *Starmerella bombicola, Meyerozyma guilliermondii, Pichia occidentalis, Monascus purpureus*, and/or *Acremonium chrysogenum*. More description of non-limiting examples of yeast can be found, for example, in US 2021/0315952 and WO 2021/163148, the content of each of which is incorporated by reference in its entirety for all purposes.

Antimethanogenic Compounds Obtained from Bacteria

In some embodiments, the antimethanogenic compound(s) is obtained from a bacterium. In some embodiments, the bacterium is one or more *Bacillus* spp. bacteria. In some embodiments, the *Bacillus* spp. are *B. amyloliquefaciens, B. subtilis* and/or *B. licheniformis*. More description of non-limiting examples of bacteria can be found, for example, in US 2021/0315952 and WO 2021/163148, the content of each of which is incorporated by reference in its entirety for all purposes.

In some embodiments the antimethanogenic compounds(s) is obtained from cyanobacteria. In some embodiments the antimethanogenic compounds(s) is obtained from a cyanobacteria of the genus *Arthrospira*. In some embodiments the antimethanogenic compounds(s) is obtained from *Arthrospira platensis* or *Arthrospira* maxima. In some embodiments the antimethanogenic compounds(s) is obtained from *spirulina*.

*Spirulina* is high in gamma-linolenic acid, and can, in some embodiments, decrease methane production while increasing propionate synthesis (see Liang Y et al. Effects of *spirulina* supplementation on lipid metabolism disorder, oxidative stress caused by high-energy dietary in Hu sheep. Meat Sci. (2020) and Li et al. Effects of dietary linseed oil and propionate precursors on ruminal microbial community, composition, and diversity in yanbian yellow cattle. *PLoS ONE*. (2015)).

Antimethanogenic Compounds Obtained from Engineered Organisms

In some embodiments, the antimethanogenic compound is obtained from a genetically engineered microorganism. Methods of cloning and expressing genes are well known in the art. For example, vanadium bromoperoxidase from the marine red alga *Corallina officinalis* has been cloned and heterologously expressed in *Escherichia coli*. The recombinant vanadium bromoperoxidase behaved similarly to native vanadium bromoperoxidase from the alga (Carter J N, et al. Reactivity of recombinant and mutant vanadium bromoperoxidase from the red alga *Corallina officinalis*. J Inorg Biochem. 2002 Jul. 25; 91(1):59-69).

In another example, a bromoperoxidase from macro-alga *Corallina pilulifera* was cloned and expressed in *E. coli* (Shimonishi M, et al., Cloning and expression of the gene for a vanadium-dependent bromoperoxidase from a marine macro-alga, *Corallina pilulifera*. FEBS Lett. 1998 May 22; 428(1-2):105-10).

Synthetic Antimethanogenic Compounds

In some embodiments, the antimethanogenic compound(s) is a synthetic. In some embodiments, the antimethanogenic compound is a statin. The term "statin" refers to a class of compounds that is known in the art as inhibitors of HMG-CoA reductase used as lipid lowering agents. In some embodiments, the antimethanogenic statin is selected from atorvastatin, cerivastatin, dalvastatin, eptastatin, fluindostatin, fluvastatin, lovastatin, mevastatin, pitavastatin, pravastatin, rosuvastatin, simvastatin, velostatin, and pharmaceutically acceptable salts, stereoisomers, or prodrug derivatives thereof. In some embodiments, the antimethanogenic statin is lovastatin, or its pharmaceutically acceptable salts, stereoisomers, or prodrug derivatives thereof. Further descriptions of antimethanogenic statin can be found, for example, in US 2018/0289816, the content of which is incorporated by reference in its entirety for all purposes.

In some embodiments, the antimethanogenic compound comprises nitrate ion. In some embodiments, the antimethanogenic compound is calcium nitrate tetrahydrate [Ca(NO$_3$)$_2$·4H$_2$O], calcium nitrate anhydrous [Ca(NO$_3$)$_2$], magnesium nitrate [Mg(NO$_3$)$_2$·6H$_2$O], sodium nitrate (NaNO$_3$), potassium nitrate (KNO$_3$) and ammonium nitrate (NH$_4$NO$_3$), cal-urea nitrate [Ca(NO$_3$)$_2$·4CO(NH$_2$)$_2$], the double salt of ammonium sulfate and nitrate, or a combination thereof. Further descriptions of nitrate ion containing antimethanogenic compounds can be found, for example, in US 2016/0165928, the content of which is incorporated by reference in its entirety for all purposes.

Vapor Pressures of Exemplary Antimethanogenic Compounds

Halogenated compounds such as bromoform are highly volatile. Examples of antimethanogenic compounds and their respective vapor pressures in pure form, in kPa at 20° C. (unless otherwise indicated) are shown below in Table 1.

TABLE 1

Vapor pressures of exemplary antimethanogenic compounds

| Antimethanogenic compound | Vapor pressure (kPa) |
|---|---|
| Bromoform | 0.67 |
| Chloroform | 212 mmHg |
| Iodoform | 0.04 mmHg |
| Methyl bromide | 1893 mmHg |
| Methyl chloride | 573 at 25° C. |
| Methyl iodide | 50 |
| Methyl fluoride | 3300 at 21° C. |
| Bromodichloromethane | 6.6 |
| Trichlorethylene | 7.8 |
| Fluoroform | 4000 |
| Dibromomethane | 4.7 |

Carriers

In one embodiment, the compositions disclosed herein comprise an antimethanogenic compound, and a liquid (e.g., water-soluble) carrier. In some embodiments, the carrier is a solvent. In some embodiments, the water-soluble carrier has a vapor pressure that is less than or equal to the vapor pressure of the antimethanogenic compound. In other embodiments, the water-soluble carrier has a vapor pressure greater than or equal to the vapor pressure of the antimethanogenic compound.

In some embodiments, the antimethanogenic compound is bromoform and the carrier has a vapor pressure of less than 0.67 kPa. In some embodiments, the antimethanogenic compound is chloroform and the carrier has a vapor pressure of less than 212 kPa. In some embodiments, the antimethanogenic compound is iodoform and the carrier has a vapor pressure of less than 0.0053 kPa (0.04 mmHg). In some embodiments, iodoform can be in a carrier with any vapor pressure. In some embodiments, the antimethanogenic compound is methyl bromide and the carrier has a vapor pressure of less than 1893 kPa. In some embodiments, the antimethanogenic compound is methyl chloride and the carrier has a vapor pressure of less than 573 kPa. In some embodiments, the antimethanogenic compound is methyl iodide and the carrier has a vapor pressure of less than 50 kPa. In some embodiments, the antimethanogenic compound is methyl fluoride and the carrier has a vapor pressure of less than 3300 kPa. In some embodiments, the antimethanogenic compound is bromodichloromethane and the carrier has a vapor pressure of less than 6.6 kPa. In some embodiments, the antimethanogenic compound is trichlorethylene and the carrier has a vapor pressure of less than 7.8 kPa. In some embodiments, the antimethanogenic compound is fluoroform and the carrier has a vapor pressure of less than 4000 kPa. In some embodiments, the antimethanogenic compound is dibromomethane and the carrier has a vapor pressure of less than 4.7 kPa.

In some embodiments the compositions comprise more than one antimethanogenic compound. In some embodiments the multi-antimethanogenic compound compositions comprise a carrier with lower vapor pressure than the antimethanogenic compound with the lowest vapor pressure. In some embodiments the carrier has a vapor pressure that is lower than the average vapor pressures of the antimethanogenic compounds in the composition.

In another embodiment, the compositions disclosed herein have a water-soluble carrier with an approximate vapor pressure of less than 1 kPa at between 20° C.-25° C. In some aspects, the carrier has a vapor pressure of less than 0.5 kPa. In some aspects, the carrier has an approximate vapor pressure of less than 100 Pa. In some aspects, the carrier has an approximate vapor pressure of less than 50 Pa.

In some aspects, the compositions disclosed herein have a non-toxic carrier that is a water-soluble alcohol. In some aspects, the carrier is selected from Table 2. In some aspects, the compositions disclosed herein comprise a non-toxic carrier that is a glycol. In some aspects, the glycol is selected from propylene glycol, dipropylene glycol, triethylene glycol, and combinations thereof. In some embodiments, the carrier has low-toxicity. In some embodiments, the carrier is diethylene glycol.

The present disclosure provides for use of antimethanogenic compounds in water soluble carriers to facilitate administration of antimethanogenic compounds via animal water sources. In some embodiments, the carrier contains a lower vapor pressure.

Use of water-soluble carriers present many benefits. For example, in some embodiments, the presently disclosed formulations comprising antimethanogenic compounds and water-soluble carriers facilitates further product formulation, by enabling mixing with other water-soluble ingredients.

In some embodiments, the presently disclosed formulations comprising antimethanogenic compounds and water-soluble carriers improve the speed and/or consistency of administration to ruminants. The inventors unexpectedly discovered that administration of antimethanogenic compounds in water-soluble liquid carriers improved dosing compared to oil. Without wishing to be bound by any one theory, the inventors hypothesize that water-soluble carriers mix better in the ruminant's stomach, and are absorbed and/or take effect at a faster rate. In some embodiments, the presently disclosed formulations are valuable in achieving higher effective dosages for ruminants, compared to other non-water-soluble formulations, which may grow in size, but do not reach higher rates of absorption in the ruminant.

In some embodiments, the non-toxic carrier is approved as an additive for animal feed. In some embodiments, the non-toxic carrier is beneficial for the ruminant animal.

In some embodiments, the carrier is able to capture or extract secondary antimethanogenic compounds from solid, liquid or gas phase (e.g. of seaweed or other material/chemical).

Examples of carriers (or water-soluble solvents) and their respective vapor pressures are shown in Table 2. Values are provided in kPa at between 20° C.-25° C. unless otherwise indicated.

TABLE 2

Example carriers and their vapor pressures

| Carrier/water soluble carrier | Vapor Pressure (kPa unless otherwise noted) |
|---|---|
| Acetic acid | 2.1 |
| Acetic acid anhydride | 0.68 |
| Acetone | 30 |
| Allyl alcohol | 2.3 |
| Allyl chloride | 40 |
| Amyl acetate | 0.47 |
| Amyl alcohol (1-pentanol) | 0.6 |
| Aniline | 0.09 |
| Beer | 2.4 |
| Benzene | 14 |

TABLE 2-continued

Example carriers and their vapor pressures

| Carrier/water soluble carrier | Vapor Pressure (kPa unless otherwise noted) |
|---|---|
| Benzyl alcohol | 0.013 |
| Bromine | 28 |
| Butanediol (1,4-Butanediol) | 0.0014 |
| Butanetriol (1,2,4-Butanetriol) | 2 |
| Butyl acetate | 1.5 |
| Butyl alcohol, 1-butanol | 0.93 |
| Butyl butyrate | 10.34 mmHg |
| Butyl propionate | 0.38 |
| 2-butanol | 1.7 |
| Butyric acid | 0.43 |
| Carbon disulphide | 48 |
| Carbon tetrachloride | 15.3 |
| Cyclohexanol | 0.9 |
| Cyclohexanone | 0.67 |
| Diethylene glycol | 2.7 Pa |
| Dimethyl sulfoxide | 59.4 Pa |
| Dipropylene glycol | 0.32 mmHg |
| Ethyl acetate | 14 |
| Ethyl alcohol (ethanol) | 12.4 |
| Ethyl butyrate | 12.8 mmHg |
| Ethyl glycol | 0.7 |
| Ethyl propionate | 35.8 mmHg |
| Ethyl pyruvate | 0.24 |
| Ethylene carbonate | 0.0098 mmHg |
| Ethylene glycol | 0.007 |
| Formic acid | 5.7 |
| Furfurol, 2-Furaldehyde | 0.3 |
| Glycerin | 0.01 Pa |
| Gelatin | |
| Heptane | 6 |
| Hexane | 17.6 |
| Hexanol | 0.124 |
| Isopropyl alcohol (rubbing alcohol) | 4.4 |
| Isopropyl acetate | 47 mmHg |
| Isopropyl butyrate | 6 mmHg |
| Isopropyl propionate | 21.6 mmHg |
| Isobutanol | 0.96 |
| Kerosene | 0.7 |
| Methyl acetate | 28.8 |
| Methyl butyrate | 40 mmHg at 30° C. |
| Methyl propionate | 11.2 |
| Methyl pyruvate | 1.0 |
| Methyl alcohol, methanol | 16.9 |
| 2-Methylbutanoic acid | 0.067 |
| Methylene chloride, dichloromethane | 58 |
| Milk | 2.4 |
| Nitrobenzene | 0.03 |
| Nonane | 0.6 |
| Octane | 1.9 |
| Pentane | 58 |
| Pentanediol (1,5-Pentanediol) | 0.0039 mmHg |
| Pentanetriol (1,2,5-Pentanetriol) | 0.000026 mmHg |
| Phenol | 0.05 |
| Propyl acetate | 3.3 |
| Propyl butyrate | 7.26 |
| Propyl propionate | 1.43 |
| Propylene glycol | 10.6 pa |
| Propanol | 2.8 |
| Propionic acid | 0.47 |
| Propylene carbonate | 0.045 mmHg |
| Sea water | 2.4 |
| Styrene | 0.85 |
| Tert-butanol | 5.6 |
| Tetrachloroethane | 0.7 |
| Tetrachloroethylene | 2.5 |
| Tetrahydrofuran | 21.3 |
| Toluene | 3.8 |
| Triacetin | 0.0025 mmHg |
| Trichloroethylene | 9.2 |
| Triethylene glycol | 0.0013 mmHg |
| Water | 2.4 |

Compositions

The compositions of the disclosure are in a water-soluble format, which allows for both homogenous mixing and quick release of the antimethanogenic compound. With effective release and even mixing, the compositions of the present disclosure decrease the chances of overdosing the supplement (e.g. from over-administration in attempts to adjust for delayed release). Additionally, the compositions of the present disclosure allow for higher concentrations of the antimethanogenic compound(s), leading to a smaller dose and/or reduced dosing frequency.

In some embodiments, the compositions of the present disclosure allow for higher doses within a smaller format. For example, in some embodiments, the compositions of the present disclosure comprise 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2100 mg, 2200 mg, 2300 mg, 2400 mg, 2500 mg, 2600 mg, 2700 mg, 2800 mg, 2900 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500 mg, 10000 mg, 10500 mg, 11000 mg, 11500 mg, 12000 mg, 12500 mg, 13000 mg, 13500 mg, 14000 mg, 14500 mg, 15000 mg, 15500 mg, 16000 mg, 16500 mg, 17000 mg, 17500 mg, 18000 mg, 18500 mg, 19000 mg, 19500 mg, 20000 mg, 20500 mg, 21000 mg, 21500 mg, 22000 mg, 22500 mg, 23000 mg, 23500 mg, 24000 mg, 24500 mg, 25000 mg, 25500 mg, 26000 mg, 26500 mg, 27000 mg, 27500 mg, 28000 mg, 28500 mg, 29000 mg, 29500 mg, 30000 mg of antimethanogenic compound in a single-dose format. Moreover, in some embodiments, compositions of the present disclosure allow such doses to be readily absorbed (take effect) by a ruminant animal within 1, 2, 3, 4, 5, 6, 7, 8, 9, 10, 11, or 12 hours. In some embodiments, the compositions of the disclosure comprise an antimethanogenic compound selected from methyl bromide, methyl chloride, methyl iodide, methyl fluoride, bromodichloromethane, trichlorethylene, bromoform, chloroform, iodoform, fluoroform, dibromomethane, and combinations thereof.

In some embodiments, the antimethanogenic compound is a synthetic. In some embodiments, the antimethanogenic compound is extracted from an organism.

In some embodiments, the compositions disclosed here have an antimethanogenic compound at a concentration of at least 0.1 mg/100 g of carrier. In some embodiments, the antimethanogenic compound has a concentration of at least 0.1 mg/100 g of carrier, at least 0.5 mg/100 g of carrier, at least 1 mg/100 g of carrier, at least 5 mg/100 g of carrier, at least 10 mg/100 g of carrier, at least 50 mg/100 g of carrier, at least 100 mg/100 g of carrier, at least 500 mg/100 g of carrier, at least 1 g/100 g of carrier, at least 5 g/100 g of carrier, at least 10 g/100 g of carrier, or at least 50 g/100 g of carrier. In some embodiments, the antimethanogenic compound has a concentration of at least 50 g per 100 g of carrier. In some embodiments, the antimethanogenic compound has a concentration of at least 55 g/100 g of carrier, at least 60 g/100 g of carrier, at least 65 g/100 g of carrier, at least 70 g/100 g of carrier, at least 75 g/100 g of carrier, at least 80 g/100 g of carrier, at least 85 g/100 g of carrier, at least 90 g/100 g of carrier, at least 95 g/100 g of carrier, or at least 100 g/100 g of carrier, at least 110 g/100 g of carrier, at least 120 g/100 g of carrier, at least 130 g/100 g of carrier, at least 140 g/100 g carrier, at least 150 g/100 g carrier, at least 160 g/100 g of carrier, at least 170 g/100 g carrier, at least 180 g/100 g carrier, at least 190 g/100 g of carrier, or at least 200 g/100 g of carrier.

In some embodiments, the antimethanogenic compound has a concentration of between 0.1 mg-0.5 mg, between 0.1 mg-1 mg, between 0.1 mg-5 mg, between 0.1 mg-10 mg, between 0.1 mg-50 mg, between 0.1 mg-100 mg, between 0.1 mg-500 mg, between 0.1 mg-1 g, between 0.1 mg-5 g, between 0.1 mg-10 g, between 0.1 mg-50 g, between 0.1 mg-100 g, between 0.1 mg-200 g, between 0.5 mg-1 mg, between 0.5 mg-5 mg, between 0.5 mg-10 mg, between 0.5 mg-50 mg, between 0.5 mg-100 mg, between 0.5 mg-500 mg, between 0.5 mg-1 g, between 0.5 mg-5 g, between 0.5 mg-10 g, between 0.5 mg-50 g, between 0.5 mg-100 g, between 0.5 mg-200 g, between 1 mg-5 mg, between 1 mg-10 mg, between 1 mg-50 mg, between 1 mg-100 mg, between 1 mg-500 mg, between 1 mg-1 g, between 1 mg-5 g, between 1 mg-10 g, between 1 mg-50 g, between 1 mg-100 g, between 1 mg-200 g, between 5 mg-10 mg, between 5 mg-50 mg, between 5 mg-100 mg, between 5 mg-500 mg, between 5 mg-1 g, between 5 mg-5 g, between 5 mg-10 g, between 5 mg-50 g, between 5 mg-100 g, between 5 mg-200 g, between 10 mg-50 mg, between 10 mg-100 mg, between 10 mg-500 mg, between 10 mg-1 g, between 10 mg-5 g, between 10 mg-10 g, between 10 mg-50 g, between 10 mg-100 g, between 10 mg-200 g, between 50 mg-100 mg, between 50 mg-500 mg, between 50 mg-1 g, between 50 mg-5 g, between 50 mg-10 g, between 50 mg-50 g, between 50 mg-100 g, between 50 mg-200 g, between 100 mg-500 mg, between 100 mg-1 g, between 100 mg-5 g, between 100 mg-10 g, between 100 mg-50 g, between 100 mg-100 g, between 100 mg-200 g, between 500 mg-1 g, between 500 mg-5 g, between 500 mg-10 g, between 500 mg-50 g, between 500 mg-100 g, between 500 mg-200 g, between 1 g-5 g, between 1 g-10 g, between 1 g-50 g, between 1 g-100 g, between 1 g-200 g, between 5 g-10 g, between 5 g-50 g, between 5 g-100 g, between 5 g-200 g, between 10 g-50 g, between 10 g-100 g, between 10 g-200 g, between 50 g-100 g, between 50 g-200 g, or between 100 g-200 g, per 100 g of carrier.

TABLE 3

Example Compositions

| Antimethanogenic compound(s) | Carrier | Concentration range (per 100 g of carrier) |
|---|---|---|
| Bromoform | Acetic acid + water | ≥0.1 mg |
| Chloroform | Acetic acid + water | ≥0.1 mg |
| Iodoform | Acetic acid + water | ≥0.1 mg |
| Methyl bromide | Acetic acid + water | ≥0.1 mg |
| Methyl chloride | Acetic acid + water | ≥0.1 mg |
| Methyl fluoride | Acetic acid + water | ≥0.1 mg |
| Methyl iodide | Acetic acid + water | ≥0.1 mg |
| Bromodichloromethane | Acetic acid + water | ≥0.1 mg |
| Trichlorethylene | Acetic acid + water | ≥0.1 mg |
| Fluoroform | Acetic acid + water | ≥0.1 mg |
| Dibromomethane | Acetic acid + water | ≥0.1 mg |
| Bromoform | Diethylene glycol | ≥0.1 mg |
| Chloroform | Diethylene glycol | ≥0.1 mg |
| Iodoform | Diethylene glycol | ≥0.1 mg |
| Methyl bromide | Diethylene glycol | ≥0.1 mg |
| Methyl chloride | Diethylene glycol | ≥0.1 mg |
| Methyl fluoride | Diethylene glycol | ≥0.1 mg |
| Methyl iodide | Diethylene glycol | ≥0.1 mg |
| Bromodichloromethane | Diethylene glycol | ≥0.1 mg |
| Trichlorethylene | Diethylene glycol | ≥0.1 mg |
| Fluoroform | Diethylene glycol | ≥0.1 mg |
| Dibromomethane | Diethylene glycol | ≥0.1 mg |
| Bromoform | Dipropylene glycol | ≥0.1 mg |

TABLE 3-continued

Example Compositions

| Antimethanogenic compound(s) | Carrier | Concentration range (per 100 g of carrier) |
|---|---|---|
| Chloroform | Dipropylene glycol | ≥0.1 mg |
| Iodoform | Dipropylene glycol | ≥0.1 mg |
| Methyl bromide | Dipropylene glycol | ≥0.1 mg |
| Methyl chloride | Dipropylene glycol | ≥0.1 mg |
| Methyl fluoride | Dipropylene glycol | ≥0.1 mg |
| Methyl iodide | Dipropylene glycol | ≥0.1 mg |
| Bromodichloromethane | Dipropylene glycol | ≥0.1 mg |
| Trichlorethylene | Dipropylene glycol | ≥0.1 mg |
| Fluoroform | Dipropylene glycol | ≥0.1 mg |
| Dibromomethane | Dipropylene glycol | ≥0.1 mg |
| Bromoform | Propylene glycol | ≥0.1 mg |
| Chloroform | Propylene glycol | ≥0.1 mg |
| Iodoform | Propylene glycol | ≥0.1 mg |
| Methyl bromide | Propylene glycol | ≥0.1 mg |
| Methyl chloride | Propylene glycol | ≥0.1 mg |
| Methyl fluoride | Propylene glycol | ≥0.1 mg |
| Methyl iodide | Propylene glycol | ≥0.1 mg |
| Bromodichloromethane | Propylene glycol | ≥0.1 mg |
| Trichlorethylene | Propylene glycol | ≥0.1 mg |
| Fluoroform | Propylene glycol | ≥0.1 mg |
| Dibromomethane | Propylene glycol | ≥0.1 mg |
| Bromoform | Triethylene glycol | ≥0.1 mg |
| Chloroform | Triethylene glycol | ≥0.1 mg |
| Iodoform | Triethylene glycol | ≥0.1 mg |
| Methyl bromide | Triethylene glycol | ≥0.1 mg |
| Methyl chloride | Triethylene glycol | ≥0.1 mg |
| Methyl fluoride | Triethylene glycol | ≥0.1 mg |
| Methyl iodide | Triethylene glycol | ≥0.1 mg |
| Bromodichloromethane | Triethylene glycol | ≥0.1 mg |
| Trichlorethylene | Triethylene glycol | ≥0.1 mg |
| Fluoroform | Triethylene glycol | ≥0.1 mg |
| Dibromomethane | Triethylene glycol | ≥0.1 mg |

In some embodiments, the water-soluble alcohol is propylene glycol and the antimethanogenic compound is bromoform. In some embodiments, the carrier is propylene glycol, the antimethanogenic compound is bromoform, and the bromoform has a concentration of at least 0.1 mg per 100 mL of propylene glycol. In some embodiments, the bromoform has a concentration of at least 0.1 mg/100 mL of propylene glycol, at least 0.5 mg/100 mL of propylene glycol, at least 1 mg/100 mL of propylene glycol, at least 5 mg/100 mL of propylene glycol, at least 10 mg/100 mL of propylene glycol, at least 50 mg/100 mL of propylene glycol, at least 100 mg/100 mL of propylene glycol, at least 500 mg/100 mL of propylene glycol, at least 1 g/100 mL of propylene glycol, at least 5 g/100 mL of propylene glycol, at least 10 g/100 mL of propylene glycol, or at least 50 g/100 mL of propylene glycol. In some embodiments, the bromoform has a concentration of at least 50 g per 100 mL of propylene glycol. In some embodiments, the bromoform has a concentration of at least 55 g/100 mL of propylene glycol, at least 60 g/100 mL of propylene glycol, at least 65 g/100 mL of propylene glycol, at least 70 g/100 mL of propylene glycol, at least 75 g/100 mL of propylene glycol, at least 80 g/100 mL of propylene glycol, at least 85 g/100 mL of propylene glycol, at least 90 g/100 mL of propylene glycol, at least 95 g/100 mL of propylene glycol, at least 100 g/100 mL of propylene glycol, at least 110 g/100 g of propylene glycol, at least 120 g/100 g of propylene glycol, at least 130 g/100 g of propylene glycol, at least 140 g/100 g propylene glycol, at least 150 g/100 g propylene glycol, at least 160 g/100 g of propylene glycol, at least 170 g/100 g propylene glycol, at least 180 g/100 g propylene glycol, at least 190 g/100 g of propylene glycol, or at least 200 g/100 g of propylene glycol.

In some embodiments, the bromoform has a concentration of between 0.1 mg-0.5 mg, between 0.1 mg-1 mg, between 0.1 mg-5 mg, between 0.1 mg-10 mg, between 0.1 mg-50 mg, between 0.1 mg-100 mg, between 0.1 mg-500 mg, between 0.1 mg-1 g, between 0.1 mg-5 g, between 0.1 mg-10 g, between 0.1 mg-50 g, between 0.1 mg-100 g, between 0.1 mg-200 g, between 0.5 mg-1 mg, between 0.5 mg-5 mg, between 0.5 mg-10 mg, between 0.5 mg-50 mg, between 0.5 mg-100 mg, between 0.5 mg-500 mg, between 0.5 mg-1 g, between 0.5 mg-5 g, between 0.5 mg-10 g, between 0.5 mg-50 g, between 0.5 mg-100 g, between 0.5 mg-200 g, between 1 mg-5 mg, between 1 mg-10 mg, between 1 mg-50 mg, between 1 mg-100 mg, between 1 mg-500 mg, between 1 mg-1 g, between 1 mg-5 g, between 1 mg-10 g, between 1 mg-50 g, between 1 mg-100 g, between 1 mg-200 g, between 5 mg-10 mg, between 5 mg-50 mg, between 5 mg-100 mg, between 5 mg-500 mg, between 5 mg-1 g, between 5 mg-5 g, between 5 mg-10 g, between 5 mg-50 g, between 5 mg-100 g, between 5 mg-200 g, between 10 mg-50 mg, between 10 mg-100 mg, between 10 mg-500 mg, between 10 mg-1 g, between 10 mg-5 g, between 10 mg-10 g, between 10 mg-50 g, between 10 mg-100 g, between 10 mg-200 g, between 50 mg-100 mg, between 50 mg-500 mg, between 50 mg-1 g, between 50 mg-5 g, between 50 mg-10 g, between 50 mg-50 g, between 50 mg-100 g, between 50 mg-200 g, between 100 mg-500 mg, between 100 mg-1 g, between 100 mg-5 g, between 100 mg-10 g, between 100 mg-50 g, between 100 mg-100 g, between 100 mg-200 g, between 500 mg-1 g, between 500 mg-5 g, between 500 mg-10 g, between 500 mg-50 g, between 500 mg-100 g, between 500 mg-200 g, between 1 g-5 g, between 1 g-10 g, between 1 g-50 g, between 1 g-100 g, between 1 g-200 g, between 5 g-10 g, between 5 g-50 g, between 5 g-100 g, between 5 g-200 g, between 10 g-50 g, between 10 g-100 g, between 10 g-200 g, between 50 g-100 g, between 50 g-200 g, or between 100 g-200 g, per 100 mL of propylene glycol.

In some embodiments, the carrier is propylene glycol, the antimethanogenic compound is chloroform, and the chloroform has a concentration of at least 0.1 mg/100 mL of propylene glycol. In some embodiments, the chloroform has a concentration of at least 0.1 mg/100 mL of propylene glycol, at least 0.5 mg/100 mL of propylene glycol, at least 1 mg/100 mL of propylene glycol, at least 5 mg/100 mL of propylene glycol, at least 10 mg/100 mL of propylene glycol, at least 50 mg/100 mL of propylene glycol, at least 100 mg/100 mL of propylene glycol, at least 500 mg/100 mL of propylene glycol, at least 1 g/100 mL of propylene glycol, at least 5 g/100 mL of propylene glycol, at least 10 g/100 mL of propylene glycol, or at least 50 g/100 mL of propylene glycol. In some embodiments, the chloroform has a concentration of at least 50 g per 100 mL of propylene glycol. In some embodiments, the chloroform has a concentration of at least 55 g/100 mL of propylene glycol, at least 60 g/100 mL of propylene glycol, at least 65 g/100 mL of propylene glycol, at least 70 g/100 mL of propylene glycol, at least 75 g/100 mL of propylene glycol, at least 80 g/100 mL of propylene glycol, at least 85 g/100 mL of propylene glycol, at least 90 g/100 mL of propylene glycol, at least 95 g/100 mL of propylene glycol, or at least 100 g/100 mL of propylene glycol, at least 110 g/100 g of propylene glycol, at least 120 g/100 g of propylene glycol, at least 130 g/100 g of propylene glycol, at least 140 g/100 g propylene glycol, at least 150 g/100 g propylene glycol, at least 160 g/100 g of propylene glycol, at least 170 g/100 g propylene glycol, at least 180 g/100 g propylene glycol, at least 190 g/100 g of propylene glycol, or at least 200 g/100 g of propylene glycol.

In some embodiments, the chloroform has a concentration of between 0.1 mg-0.5 mg, between 0.1 mg-1 mg, between 0.1 mg-5 mg, between 0.1 mg-10 mg, between 0.1 mg-50 mg, between 0.1 mg-100 mg, between 0.1 mg-500 mg, between 0.1 mg-1 g, between 0.1 mg-5 g, between 0.1 mg-10 g, between 0.1 mg-50 g, between 0.1 mg-100 g, between 0.1 mg-200 g, between 0.5 mg-1 mg, between 0.5 mg-5 mg, between 0.5 mg-10 mg, between 0.5 mg-50 mg, between 0.5 mg-100 mg, between 0.5 mg-500 mg, between 0.5 mg-1 g, between 0.5 mg-5 g, between 0.5 mg-10 g, between 0.5 mg-50 g, between 0.5 mg-100 g, between 0.5 mg-200 g, between 1 mg-5 mg, between 1 mg-10 mg, between 1 mg-50 mg, between 1 mg-100 mg, between 1 mg-500 mg, between 1 mg-1 g, between 1 mg-5 g, between 1 mg-10 g, between 1 mg-50 g, between 1 mg-100 g, between 1 mg-200 g, between 5 mg-10 mg, between 5 mg-50 mg, between 5 mg-100 mg, between 5 mg-500 mg, between 5 mg-1 g, between 5 mg-5 g, between 5 mg-10 g, between 5 mg-50 g, between 5 mg-100 g, between 5 mg-200 g, between 10 mg-50 mg, between 10 mg-100 mg, between 10 mg-500 mg, between 10 mg-1 g, between 10 mg-5 g, between 10 mg-10 g, between 10 mg-50 g, between 10 mg-100 g, between 10 mg-200 g, between 50 mg-100 mg, between 50 mg-500 mg, between 50 mg-1 g, between 50 mg-5 g, between 50 mg-10 g, between 50 mg-50 g, between 50 mg-100 g, between 50 mg-200 g, between 100 mg-500 mg, between 100 mg-1 g, between 100 mg-5 g, between 100 mg-10 g, between 100 mg-50 g, between 100 mg-100 g, between 100 mg-200 g, between 500 mg-1 g, between 500 mg-5 g, between 500 mg-10 g, between 500 mg-50 g, between 500 mg-100 g, between 500 mg-200 g, between 1 g-5 g, between 1 g-10 g, between 1 g-50 g, between 1 g-100 g, between 1 g-200 g, between 5 g-10 g, between 5 g-50 g, between 5 g-100 g, between 5 g-200 g, between 10 g-50 g, between 10 g-100 g, between 10 g-200 g, between 50 g-100 g, between 50 g-200 g, or between 100 g-200 g, per 100 mL of propylene glycol.

In some embodiments, the carrier is propylene glycol, the antimethanogenic compound is iodoform, and the iodoform has a concentration of at least 0.1 g/100 mL of propylene glycol. In some embodiments, the iodoform has a concentration of at least 0.1 mg/100 mL of propylene glycol, at least 0.5 mg/100 mL of propylene glycol, at least 1 mg/100 mL of propylene glycol, at least 5 mg/100 mL of propylene glycol, at least 10 mg/100 mL of propylene glycol, at least 50 mg/100 mL of propylene glycol, at least 100 mg/100 mL of propylene glycol, at least 500 mg/100 mL of propylene glycol, at least 1 g/100 mL of propylene glycol, at least 5 g/100 mL of propylene glycol, at least 10 g/100 mL of propylene glycol, or at least 50 g/100 mL of propylene glycol. In some embodiments, the iodoform has a concentration of at least 50 g per 100 mL of propylene glycol. In some embodiments, the iodoform has a concentration of at least 55 g/100 mL of propylene glycol, at least 60 g/100 mL of propylene glycol, at least 65 g/100 mL of propylene glycol, at least 70 g/100 mL of propylene glycol, at least 75 g/100 mL of propylene glycol, at least 80 g/100 mL of propylene glycol, at least 85 g/100 mL of propylene glycol, at least 90 g/100 mL of propylene glycol, at least 95 g/100 mL of propylene glycol, at least 100 g/100 mL of propylene glycol, at least 110 g/100 g of propylene glycol, at least 120 g/100 g of propylene glycol, at least 130 g/100 g of propylene glycol, at least 140 g/100 g propylene glycol, at least 150 g/100 g propylene glycol, at least 160 g/100 g of propylene glycol, at least 170 g/100 g propylene glycol, at least 180 g/100 g propylene glycol, at least 190 g/100 g of propylene glycol, or at least 200 g/100 g of propylene glycol.

In some embodiments, the iodoform has a concentration of between 0.1 mg-0.5 mg, between 0.1 mg-1 mg, between 0.1 mg-5 mg, between 0.1 mg-10 mg, between 0.1 mg-50 mg, between 0.1 mg-100 mg, between 0.1 mg-500 mg, between 0.1 mg-1 g, between 0.1 mg-5 g, between 0.1 mg-10 g, between 0.1 mg-50 g, between 0.1 mg-100 g, between 0.1 mg-200 g, between 0.5 mg-1 mg, between 0.5 mg-5 mg, between 0.5 mg-10 mg, between 0.5 mg-50 mg, between 0.5 mg-100 mg, between 0.5 mg-500 mg, between 0.5 mg-1 g, between 0.5 mg-5 g, between 0.5 mg-10 g, between 0.5 mg-50 g, between 0.5 mg-100 g, between 0.5 mg-200 g, between 1 mg-5 mg, between 1 mg-10 mg, between 1 mg-50 mg, between 1 mg-100 mg, between 1 mg-500 mg, between 1 mg-1 g, between 1 mg-5 g, between 1 mg-10 g, between 1 mg-50 g, between 1 mg-100 g, between 1 mg-200 g, between 5 mg-10 mg, between 5 mg-50 mg, between 5 mg-100 mg, between 5 mg-500 mg, between 5 mg-1 g, between 5 mg-5 g, between 5 mg-10 g, between 5 mg-50 g, between 5 mg-100 g, between 5 mg-200 g, between 10 mg-50 mg, between 10 mg-100 mg, between 10 mg-500 mg, between 10 mg-1 g, between 10 mg-5 g, between 10 mg-10 g, between 10 mg-50 g, between 10 mg-100 g, between 10 mg-200 g, between 50 mg-100 mg, between 50 mg-500 mg, between 50 mg-1 g, between 50 mg-5 g, between 50 mg-10 g, between 50 mg-50 g, between 50 mg-100 g, between 50 mg-200 g, between 100 mg-500 mg, between 100 mg-1 g, between 100 mg-5 g, between 100 mg-10 g, between 100 mg-50 g, between 100 mg-100 g, between 100 mg-200 g, between 500 mg-1 g, between 500 mg-5 g, between 500 mg-10 g, between 500 mg-50 g, between 500 mg-100 g, between 500 mg-200 g, between 1 g-5 g, between 1 g-10 g, between 1 g-50 g, between 1 g-100 g, between 1 g-200 g, between 5 g-10 g, between 5 g-50 g, between 5 g-100 g, between 5 g-200 g, between 10 g-50 g, between 10 g-100 g, between 10 g-200 g, between 50 g-100 g, between 50 g-200 g, or between 100 g-200 g, per 100 mL of propylene glycol.

Capsules and Other Forms of Administration

In some embodiments, the present disclosure teaches compositions for administration to ruminant animals. In some embodiments, the compositions are administered via water allotments for ruminants. In some embodiments, the compositions are administered via food allotments for ruminant animals.

In some embodiments, the compositions of the present disclosure can also be administered like a medicine, or dietary supplement. For example, in some embodiments, the compositions of the present disclosure are administered as a capsule, tincture, rapidly dissolving gel, mechanical housing, or other known delivery avenue.

In some aspects, the disclosure provides an oral capsule containing a dose of an antimethanogenic compound and a liquid (e.g. water-soluble) carrier. In some aspects, the water-soluble carrier is a water-soluble alcohol. In some aspects, the water-soluble alcohol is selected from propylene glycol, diethylene glycol, dipropylene glycol, triethylene glycol, and combinations thereof.

In some aspects, the capsule comprises a gelling agent. In some aspects, the gelling agent is selected from gelatin, modified starch, carrageenan, gellan, mannan gum, amylose, xanthan, alginates, agar, guar, gum arabic, pectin, cyclodextrin, and combinations thereof. In some aspects, the capsule comprises a gelling salt, a plasticizer, an emulsifier, a thickener, a preservative, a flavoring, a sweetener, a pigment, an opacifying agent, an anti-oxidant, or combinations thereof.

Additives

The compositions of the present disclosure may comprise any number of additives for flavoring, additional benefits for the animal, shelf life, etc.

In some embodiments, the additive comprises a vitamin and/or a mineral.

In some embodiments, the additive comprises a vitamin. In some embodiments, the vitamin comprises at least one fat-soluble vitamin and/or at least one water-soluble vitamin. In some embodiments, the fat-soluble vitamin is selected from vitamin A, vitamin D3, vitamin E, vitamin K (e.g. vitamin K3), and a combination thereof. In some embodiments, the water-soluble vitamin is selected from vitamin B12, biotin, choline, vitamin B1, vitamin B2, vitamin B6, niacin, folic acid, panthothenate (e.g. Ca-D-panthothenate), and a combination thereof. In some embodiments, the compositions of the present disclosure comprise vitamin B12.

In some embodiments, the additive comprises a mineral. In some embodiments, the mineral comprises at least one trace mineral and/or at least one macro mineral. In some embodiments, the trace mineral is selected from manganese, zinc, iron, copper, iodine, selenium, cobalt, and a combination thereof. In some embodiments, the macro mineral is selected from calcium, phosphorus, sodium, and a combination thereof.

In some embodiments, the additive comprises one or more of flavoring agents, sweetening agents, coloring agents, stabilizers, and/or enzymes.

In some embodiments, the one or more flavoring agents are selected from oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, and cinnamaldehyde glycerol acetal known as CGA.

In some embodiments, the one or more sweetening agents are selected from sucrose, glucose, saccharin, dextrose, levulose, lactose as described herein above, mannitol, sorbitol, fructose, maltose, xylitol, saccharin salts, thaumatin, aspartame, D-tryptophane, dihydrochalcones, and acesulfame and cyclamate salts, especially sodium cyclamate and sodium saccharin.

In some embodiments, the one or more colorants are selected from iron oxide, sodium chloride, potassium citrate, potassium chloride, and other edible salts.

In some embodiments, the one or more stabilizers are selected from preservatives, antioxidants, synergists and sequestrants, packaging gases, emulsifiers, thickeners, gelling agents, and humectants. Examples of emulsifiers and/or thickening agents include, for example, gelatin, cellulose ethers, starch, starch esters, starch ethers, and modified starches. In some embodiments, the one or more stabilizers increase the shelf life of the composition.

In some embodiments, the one or more enzymes are selected from amongst phytases EC 3.1.3.8 or 3.1.3.26; xylanases EC 3.2.1.8; galactanases EC 3.2.1.89; and/or beta-glucanases EC 3.2.1.4 (EC refers to Enzyme Classes according to Enzyme Nomenclature 1992 from NC-IUBMB, 1992).

Additional descriptions of additives can be found, for example, in US 2017/0273895, US 2009/0258030 and US 2005/0142169, the content of each of which is incorporated by reference in its entirety for all purposes.

Capturing and Extracting Antimethanogenic Compounds

In another embodiment, the present disclosure teaches a method of capturing antimethanogenic compounds, comprising the steps of: a) providing a first solution comprising an antimethanogenic compound in a non-water soluble carrier; b) providing a second solution comprising a water-soluble carrier selected from Table 2; c) contacting the first solution and second solution, thereby transferring antimethanogenic compound from the first solution to the second solution. In some embodiments, the non-water-soluble carrier is an oil.

In some embodiments, this permits for high quality extractions of antimethanogenic compounds into water soluble carriers. Using oil as an intermediate can be helpful in a variety of ways. First, antimethanogenic compounds are typically not highly soluble in water. For example, bromoform is only soluble at 3.19 grams per liter of water at 30 Celsius. The solubility of bromoform in propylene glycol is higher than 60 grams at the same temperature (see e.g., Example 1 of this specification).

Second, because bromoform is typically extracted from algae, using water or other water-soluble carriers that were directly contacted with the algae can result in impure extracts, with lots of other water-soluble contaminants. Removing water from an algae slurry can be expensive, given the filtering steps necessary to remove contaminants such as algae parts, potentially pathogenic microbes, and other contaminants. The inventors hypothesize that the use of an oil as an extraction intermediate may also serve to act as a barrier to metal ions and other undesirable ions (e.g. arsenic, aluminum, fluoride, and iodide ions) that may be present in an algal biomass, as these are not well absorbed by the oil. Therefore, these undesirable ions are not extracted with the antimethanogenic compounds, and would not be present in final composition comprising a water-soluble carrier. Transferring the antimethanogenic compound from oil to a water-soluble carrier is simplified due to the immiscibility of oil and the water-soluble carrier.

In some embodiments, the oil may comprise any suitable oil, including, for example, vegetable oil. In some embodiments, the oil comprises an oil selected from the group consisting of canola oil, olive oil, corn oil, mineral oil, and combinations thereof. In some embodiments, the oil is selected from soybean oil, corn oil, palm kernel oil, rapeseed oil, sunflower oil, safflower oil, coconut oil, rice bran oil, sesame oil, flaxseed oil, hemp oil, or cottonseed oil. In some embodiments, the oil is peanut oil, almond oil, beech nut oil, brazil nut oil, cashew oil, hazelnut oil, macadamia oil, mongongo nut oil, pecan oil, pine nut oil, pistachio oil, walnut oil, or pumpkin seed oil. In some embodiments, the oil is grapefruit seed oil, lemon oil, apricot oil, apple seed oil, argan oil, avocado oil, or orange oil.

In some embodiments, the non-water-soluble carrier and the water-soluble carrier are mixed at a ratio of 1:1. In some embodiments, the water-soluble carrier is able to capture at least 10% of the antimethanogenic compound from the non-water-soluble carrier. In some embodiments, the water-soluble carrier is able to capture at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, or at least 50% of the antimethanogenic compound from the non-water-soluble carrier. In some embodiments, the water-soluble carrier is able to capture at least 55%, at least 60%, at least 65%, at least 70%, at least 75%, at least 80%, at least 85%, at least 90%, or at least 95% of the antimethanogenic compound from the non-water-soluble carrier.

In another embodiment, the present disclosure teaches a method of capturing antimethanogenic gas, comprising the steps of: contacting the antimethanogenic gas with a water-soluble carrier selected from Table 2; wherein at least 10% of the antimethanogenic gas is retained within the water-soluble carrier.

In some embodiments, the method of capturing antimethanogenic gas results in at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% of the antimethanogenic gas is retained within the water-soluble carrier.

In another embodiment, the present disclosure teaches a method of extracting antimethanogenic compounds from algae, comprising the steps of: a) providing algae biomass containing an antimethanogenic compound; b) heating the algae biomass, thereby creating a heated gas above the algae biomass, said heated gas comprising the antimethanogenic compound; c) contacting the heated gas with a water-soluble carrier selected from Table 2; wherein at least 10% of the antimethanogenic compound in the heated gas is retained within the water-soluble carrier.

In some embodiments, the method of extracting an antimethanogenic compound from an algae biomass results in at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% of the antimethanogenic gas is retained within the water-soluble carrier.

In another embodiment, the present disclosure teaches a method of concentrating antimethanogenic compounds, comprising the steps of: contacting the antimethanogenic compound with a water-soluble carrier selected from Table 2; wherein the antimethanogenic compound reaches a concentration of at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9 10, 20, 30, 40, 50, or 60 milligrams of antimethanogenic compound per milliliter of water-soluble carrier.

In some embodiments, the antimethanogenic compound reaches a concentration of at least 61 mg/ml, at least 62 mg/ml, at least 63 mg/ml, at least 64 mg/ml, at least 65 mg/ml, at least 66 mg/ml, at least 67 mg/ml, at least 68 mg/ml, at least 69 mg/ml, at least 70 mg/ml, at least 71 mg/ml, at least 72 mg/ml, at least 73 mg/ml, at least 74 mg/ml, at least 75 mg/ml, at least 76 mg/ml, at least 77 mg/ml, at least 78 mg/ml, at least 79 mg/ml, at least 80 mg/ml, at least 81 mg/ml, at least 82 mg/ml, at least 83 mg/ml, at least 84 mg/ml, at least 85 mg/ml, at least 86 mg/ml, at least 87 mg/ml, at least 88 mg/ml, at least 89 mg/ml, at least 90 mg/ml, at least 91 mg/ml, at least 92 mg/ml, at least 93 mg/ml, at least 94 mg/ml, at least 95 mg/ml, at least 96 mg/ml, at least 97 mg/ml, at least 98 mg/ml, at least 99 mg/ml, or at least 100 mg/ml of water-soluble carrier.

In some embodiments, the antimethanogenic compound reaches a concentration of at least 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9 10, 20, 30, 40, 50, or 60 grams of antimethanogenic compound per milliliter of water-soluble carrier In some embodiments, the contacting includes mixing, stirring, shaking, or the like. In some embodiments, the water-soluble carrier is a glycol.

Formulations

In some embodiments, the water-soluble compositions disclosed herein may be formulated and/or incorporated into animal watering system for ruminant animals. Thus, in some embodiments, the disclosure relates to a composition as described herein and water.

In some embodiments, the compositions disclosed herein may be formulated and/or incorporated into animal feed for feeding to ruminant animals. Thus, in some embodiments, the disclosure relates to a composition as described herein and an animal feed.

In some embodiments, the water-soluble composition is added directly to the ration of food by way on adding on top (as a so-called top-dress) or by mixing into the total mixed ration. When used as a feed additive, the composition may be further formulated to enhance the flavor, nutrition, and/or shelf life. Non-limiting examples of formulations may include preservatives, antioxidants, emulsifiers, stabilising agents, acidity regulators, silage additives, sensory additives, flavours, colorants, nutritional additives such as vitamins, amino acids and trace elements, and zootechnical additives, such as digestibility enhancers and gut flora stabilizers.

In some embodiments, the compositions disclosed herein are incorporated into the manufacture of compounded animal feeds. Compounded animal feeds as used herein refers to any composition suitable for use as an animal feed and which is blended from various materials (e.g., wheat bran, rice bran, corn meal, cereal grains, such as barley, wheat, rye and oat, soybean meal, alfalfa meal, cottonseed meal, wheat powder). Compounded animal feed may be liquid, solid, or semi-solid.

In some embodiments, the compositions disclosed herein may be formulated and/or incorporated into a lick block.
Example Formulations:
Bromoform (e.g., synthetic or natural)
Bromoform (e.g., synthetic or natural) plus Vitamin B12
bromoform (e.g., synthetic or natural) plus B12 plus algae propylene glycol extract
propylene glycol with full spectrum seaweed extracts
propylene glycol with iodoform (e.g., synthetic or natural)
propylene glycol with chloroform (e.g., synthetic or natural)

In some embodiments, natural antimethanogenic compounds are extracted from algae or other organisms, as known to those of skill in the art and described in this document.
Use of the Disclosed Antimethanogenic Compositions in a Ruminant Animal Ruminant animals are those mammals in the suborder Ruminantia. Most have four-chambered stomachs and two-toed feet. The first chamber of the stomach is called the rumen and is the primary site microbial fermentation, where hard to digest plant material like cellulose is broken down. Including wild and domesticated species, there are roughly 200 species of ruminants. Example ruminants include, but are not limited to, bovine (cattle), goats, sheep, bison, giraffes, deer, elk, gazelles, antelopes, alpacas, llamas, and camels.

In some embodiments, the disclosure teaches a method of reducing enteric methane production in a ruminant animal over a short or an extended period of time comprising administering a composition disclosed herein, wherein the composition comprises an antimethanogenic compound(s).

In some embodiments, the ruminant animal supplemented with a composition of the present disclosure emit about 1%, 2%, 3%, 4%, 5%, 6%, 7%, 8%, 9%, 10% or 11% less methane than a ruminant animal not receiving the composition. In some embodiments, the ruminant animal supplemented with a composition of the present disclosure emit about 10% to 20%, 21% to 30%, 31% to 40%, 41% to 50%, 51% to 60%, 61% to 70%, 71% to 80%, 81% to 90%, 91% to 99% or 100% less methane than a ruminant animal not receiving the composition.

In some embodiments, the disclosure teaches a method for increasing feed efficiency, the method comprising administering a composition of the disclosure to a ruminant animal. Feed efficiency is represented as the feed to gain ratio (F:G), also known as the feed conversion ratio (FCR). It is a measure of an animal's efficiency in converting feed nutrients into increased body mass. Thus, a lower feed to gain ratio represents a better feed efficiency. Examples of more and less efficient feed to gain ratios are shown in Table 4 below (adapted from extension.usu.edu/4h-livestock-calculator/research/market-animal-feed-efficiency-a-tool-for-evaluating-feed-conversion). See also Cameron, M. R., et al. (2001) Growth and slaughter traits of Boer×Spanish, Boer× Angora, and Spanish goats consuming a concentrate-based diet, *J. of Animal Science,* 79(6), 1423; Claffey, et al. (2018) Effect of forage to concentrate ratio and duration of feeding on growth and feed conversion efficiency of male lambs, *Translational Animal Science,* 2(4), 419-427; Lewis, S. J., et al. (1997) Feedlot performance and carcass traits of Boer goat crosses and Spanish male kids, *Journal of Animal Science,* 75(Suppl. 1), 40; Shike, D. (2013) Beef cattle feed efficiency [Conference session], Driftless Range Beef Conference, Dubuque, IA, United States; and Stender, D. (2012) Swine feed efficiency: Influence of market weight [Fact sheet], Iowa State University.

To measure an animal's feed conversion efficiency, one must first calculate the animal's average daily gain, and the weight of the animal's daily ration. To obtain the feed conversion efficiency, the daily ration weight is divided by the average daily gain:

Daily Ration (dry matter intake–DMI)/Average Daily Gain (ADG)=Feed Conversion Efficiency.

TABLE 4

Example feed to gain ratios for different animals

| Species | Feed conversion efficiency (lb. DMI/lb.ADG) | | % Difference | Reference |
| --- | --- | --- | --- | --- |
| | More efficient | Less efficient | | |
| Cattle | 4.5 | 7.5 | 40% | Shike 2013 |
| Sheep | 4.1 | 11.7 | 65% | Claffey et al. 2018 |
| Goats | 3.9 | 10.5 | 63% | Cameron et al. 2001; Lewis et al. 1997 |

In some embodiments, the ruminant animal supplemented with a composition of the present disclosure exhibits an F:G of less than 7. In some embodiments, the ruminant animal supplemented with a composition of the present disclosure exhibits an F:G of less than 6.9, 6.8, 6.7, 6.6, 6.5, 6.4, 6.3, 6.2, 6.1, or 6.0.

In some embodiments, the ruminant animal supplemented with a composition of the present disclosure exhibits an F:G of less than 5.9, 5.8, 5.7, 5.6, 5.5, 5.4, 5.3, 5.2, 5.1, or 5.0.

In some embodiments, the ruminant animal supplemented with a composition of the present disclosure exhibits an F:G of less than 4.9, 4.8, 4.7, 4.6, 4.5, 4.4, 4.3, 4.2, 4.1, or 4.0.

In some embodiments, the ruminant animal supplemented with a composition of the present disclosure exhibits an F:G of less than 3.9, 3.8, 3.7, 3.6, 3.5, 3.4, 3.3, 3.2, 3.1, or 3.0.

In some embodiments, the ruminant animal supplemented with a composition of the present disclosure exhibits at least a 0.1% increase in feed efficiency compared to a ruminant animal that did not receive the composition. In some embodiments, the ruminant animal supplemented with a composition of the present disclosure exhibits at least a 0.2%, a 0.3%, a 0.4%, a 0.5%, a 0.6%, a 0.7%, a 0.8%, at 0.9%, or a 1% increase in feed efficiency compared to a ruminant animal that did not receive the composition.

In some embodiments, the ruminant animal supplemented with a composition of the present disclosure exhibits at least a 1%, a 2%, a 3%, a 4%, a 5%, a 6%, a 7%, an 8%, a 9%, or a 10% increase in feed efficiency compared to a ruminant animal that did not receive the composition.

In some embodiments, the ruminant animal supplemented with a composition of the present disclosure exhibits at least an 11%, a 12%, a 13%, a 14%, a 15%, a 16%, a 17%, an 18%, at 19%, or a 20% increase in feed efficiency compared to a ruminant animal that did not receive the composition.

In some embodiments, the ruminant animal supplemented with a composition of the present disclosure exhibits at least a 21%, a 22%, a 23%, a 24%, 25%, a 26%, a 27%, a 28%, at 29%, or a 30% increase in feed efficiency compared to a ruminant animal that did not receive the composition.

In some embodiments, the ruminant animal supplemented with a composition of the present disclosure exhibits at least a 31%, a 32%, a 33%, a 34%, a 35%, a 36%, a 37%, a 38%, at 39%, or a 40% increase in feed efficiency compared to a ruminant animal that did not receive the composition.

In some embodiments, the ruminant animal supplemented with a composition of the present disclosure exhibits at least a 41%, a 42%, a 43%, a 44%, a 45%, a 46%, a 47%, a 48%, at 49%, or a 50% increase in feed efficiency compared to a ruminant animal that did not receive the composition.

In some embodiments, the disclosure teaches a method for reducing cost per pound of weight gain of a market animal, the method comprising administering a composition of the disclosure to a ruminant animal. The cost per pound gained can be determined as follows: Cost per Pound offeedxFeed Efficiency=Cost per Pound of Gain. For example, if the price per pound is $0.50, and the Feed Efficiency is 3.7, then the Cost per Pound of Gain would be $1.85.

In some embodiments, the method for reducing cost per pound of weight gain of a market animal reduces the cost per pound by 1% compared to an animal that did not receive the composition. In some embodiments, the method reduces the cost per pound by 2%, 3%, 4%, 5%, 6%, 7%, 8%, 9%, 10%, 11%, 12%, 13%, 14%, or 15% compared to an animal that did not receive the composition.

In some embodiments, the method reduces the cost per pound by 16%, 17%, 18%, 19%, 20%, 21%, 22%, 23%, 24%, 25%, 26%, 27%, 28%, 29%, or 30% compared to an animal that did not receive the composition.

In some embodiments, the method reduces the cost per pound by 35%, 40%, 45%, 50%, 55%, 60%, 65%, 70%, or 75%, compared to an animal that did not receive the composition.

In some embodiments, the composition is administered in an amount between 0.01 mg and 1 mg antimethanogenic compound per kg of body weight. In some embodiments, the composition is administered in a range of between 0.1 and 1 mg antimethanogenic compound per kg of body weight.

In some embodiments, the composition is administered in an amount of 0.01 mg antimethanogenic compound per kg of body weight. In some embodiments, the composition is administered in an amount of 0.02 mg antimethanogenic compound per kg of body weight, 0.03 mg antimethanogenic compound per kg of body weight, 0.04 mg antimethanogenic compound per kg of body weight, 0.05 mg antimethanogenic compound per kg of body weight, 0.06 mg antimethanogenic compound per kg of body weight, 0.07 mg antimethanogenic compound per kg of body weight, 0.08 mg antimethanogenic compound per kg of body weight, 0.09 mg antimethanogenic compound per kg of body weight, 0.1 mg antimethanogenic compound per kg of body weight, 0.2 mg antimethanogenic compound per kg of body weight, 0.3 mg antimethanogenic compound per kg of body weight, 0.4 mg antimethanogenic compound per kg of body weight, 0.5 mg antimethanogenic compound per kg of body weight, 0.6 mg antimethanogenic compound per kg of body weight, 0.7 mg antimethanogenic compound per kg of body weight, 0.8 mg antimethanogenic compound per kg of body weight, 0.9 mg antimethanogenic compound per kg of body weight, or 1 mg antimethanogenic compound per kg of body weight.

In another embodiment, the composition disclosed herein is administered to a ruminant animal continuously, every hour, every day, every 1.5 days, every 2 days, every 3 days or every 4.5 days. In another embodiment, the composition disclosed herein is administered to a ruminant animal every 7 days. In another embodiment, the composition disclosed herein is administered to a ruminant animal every month, every 3 months, every 6 months, every year, every 2 years. In another embodiment, the composition disclosed herein is administered to a ruminant animal once per lifetime of the animal.

In some embodiments, the animal is a breed of cattle. Exemplary cattle breeds include, but are not limited to, Angus, or Aberdeen-Angus, Ayrshire, Beefmaster, Belgium Blue, Belted Galloway, Brahman, or Zebu, Brangus, British White, Brown Swiss, Charolais, Chianina, Devon, Dexter, English Longhorn, Galloway, Gloucester, Guernsey, Hereford, or Whiteface, Highland, Holstein-Friesian, Irish Moiled, Jersey, Kerry, Limousin, Luing, Milking Devon, Milking Shorthorn, Normande, Polled Hereford, Red Angus, Red Poll, Santa Gertrudis, Shorthorn, or Durham, South Devon, Simmental, Sussex, Welsh Black, and White Park.

In some embodiments the animal is selected from the group consisting of Sheep, Goats, Deer, (including reindeer), Moose, Giraffes, Bison, Antelopes (including gazelles), Camels (including dromedaries and Bactrian camels), Yaks, Muskoxen, Water buffalo, Pronghorns, Ibexes, Chamois, Saiga antelope, Gemsbok, Wildebeest, Markhor, Sable antelope.

The disclosure will be further described by way of the following examples, which are meant to serve to assist one of ordinary skill in the art in carrying out the disclosure and are not intended in any way to limit the scope of the disclosure.

EXAMPLES

The foregoing examples of the related art and limitations related therewith are intended to be illustrative and not exclusive. Other limitations of the related art will become apparent to those of skill in the art upon a reading of the specification.

Example 1—Bromoform is Highly Soluble in Propylene Glycol

To test the solubility of bromoform in propylene glycol, 10 ml propylene glycol was pipetted into a glass vial at room temperature, and 2 ml of bromoform (6.62 g) was added to it. The glass vial lid was closed and the vial shaken gently for 10 seconds. The final solution was clear, without any separation layer, indicating that all bromoform had dissolved, making the final concentration 66.2 g bromoform/100 ml propylene glycol. This is an extremely high concentration. The actual limit of solubility could be even higher, and will be tested further.

In contrast the solubility of bromoform in water is less than 0.32 g bromoform/100 ml of water. Thus, compositions of bromoform in propylene glycol can be helpful in delivering high doses of antimethanogenic substances to ruminants.

Example 2—Propylene Glycol can Extract Bromoform from Corn Oil

To test whether propylene glycol could extract antimethanogenic compounds from corn oil, propylene glycol was added to a corn oil extract containing bromoform. Specifically, 10 ml of corn oil that was previously used to extract bromoform from seaweed (containing between about 1.8-2.3 mg/g) was added to a glass vial. 10 ml of fresh propylene glycol was also added to the same vial, and the mixture was shaken for 5 min.

The mixture was then centrifuged at 5000 rpm for 10 min at room temperature to allow for separation into two layers. The top layer comprising the corn oil and the bottom layer comprising the propylene glycol were collected and submitted to a third-party lab for bromoform concentration testing.

The test report showed that the corn oil contained 1.4 mg/g bromoform, and the propylene glycol contained 0.63 mg/g bromoform. Therefore, when mixed at 1:1 ratio of corn oil and propylene glycol, the propylene glycol was able to capture about 30% of the bromoform contained within the corn oil.

Higher percentages of antimethanogenic compounds may be extracted from oils with different ratios and longer mix times.

Example 3—Propylene Glycol and Corn Oil can Capture Bromoform from a Gas Stream To determine if bromoform could be captured from a gas stream, the following experiments were conducted with corn oil and propylene glycol.

For corn oil: 0.1 ml (approximately 289 mg) bromoform was added to 1 L distilled water in a flask to make a bromoform solution. The flask was sealed with a rubber stopper and shaken to dissolve the bromoform. The flask was then coupled to an air flow at 0.1 L/min at room temperature. The outlet air was introduced to a test tube filled with 50 g corn oil (depth of 15 cm) through a 2 ml transfer pipette. This test tube was further coupled to a second test tube containing another 50 g corn oil via another air outlet, to determine how much bromoform was not captured by the first test tube.

After bubbling for 6 hours, the oil samples in test tubes 1 and 2 were collected and submitted to a third-party lab for bromoform testing. The test report showed that the first test tube contained 138000 μg/L bromoform (138000 μg/L*50 g oil/0.92 g/ml (corn oil density)=7.5 mg) and that the second test tub contained 271 μg/L bromoform (271 μg/L*50 g oil/0.92 g/ml=14.73 μg). Therefore, the bromoform capture efficiency for the corn oil was 138000/(138000+271)*100%=99.8%.

For propylene glycol: 392.95 grams of freeze dried *Gracilaria* sp. seaweed biomass containing bromoform was placed into a 1 L glass flask and heated to 60° C. in a water bath to facilitate releasing the bromoform from the algae biomass. Air was introduced to the flask at 0.1 L/min. The outlet of air flow entered a first test tube containing 60.7 g propylene glycol (16 cm depth) via a 2 ml pipette. The first test tube was coupled to a second via another 2 ml pipette. The second test tube contained 54.79 g corn oil (16 cm depth) as a second trap for bromoform. After 12 hours of air flush, both the propylene glycol and corn oil were collected and sent to a third party for bromoform testing. The test report showed that the propylene glycol contained 0.35 mg/g bromoform, and the corn oil contained 0.025 mg/g bromoform. That means the total amount of amount captured in propylene glycol and corn oil combined was 22.57 mg (60.7 g*0.35 mg/g=21.2 mg and 54.79*0.025 mg/g=1.370 mg).

Since the corn oil has a capturing efficiency of 99.8% as described above, the bromoform capturing efficiency of propylene glycol can be determined as follows: total missed bromoform from PG test tube was 1.37 mg/99.8%=1.372 mg; 21.2 mg/(21.2 mg+1.372 mg)*100%=93.9%.

Example 4—Increasing Feed Efficiency

*Charlais angus* cross cattle were randomly sorted into two separate pens of 24 cattle each and all were weighed on days 1, 7, and 14 of the testing period. Feed consumed by each pen as a whole was weighed each day. Any uneaten amount was subtracted from the amount of feed placed into the feed bunk for each pen so that the final amounts are the "fed" totals of each pen.

The ration compositions were as follows: BGNoP: 21.82% Silage, 22.47% Straw, 54.18% Barley, 1.53% L/S. BGPellet: 31.31% Silage, 17.19% Straw, 35.68% barley, 1.46% L/S 14.76% Pellets. For the experimental group, a composition comprising between 1.6-2.2 mg/g bromoform in propylene glycol was mixed with the ration right before it was fed to the cattle, at a daily dose of bromoform of 0.2% (controlled by micro machine) of total feed.

TABLE 5

| | Feed to gain | | | | | | | | | |
|---|---|---|---|---|---|---|---|---|---|---|
| | Total feed (DWI) | | Total weight (lb) | | Avg. weight (lb per animal) | | Total weight gain (lbs) | | Feed to gain | |
| Date | Control | Exp | Control | Exp | Control | Exp | Control | Exp | Control | Exp |
| May 23, 2023 | 0 | 0 | 20261 | 20097 | 844.2 | 837.4 | 0 | 0 | n/a | n/a |
| May 29, 2023 | 3880 | 4140 | 20889 | 20742 | 870.4 | 864.3 | 628 | 645 | n/a | n/a |
| Jun. 5, 2023 | 8810 | 8650 | 21379 | 21539 | 890.8 | 897.5 | 1118 | 1442 | 7.88 | 5.99 |

As shown in Table 5 above and FIG. 1, at the conclusion of the 14-day test period cattle that received the water-soluble composition of the disclosure weighed an average 897.5 lbs, whereas the cattle in the control group weighed an average of 890.8 lbs.

Additionally, after the 14-day test period, the experimental group had a feed to gain ratio of 5.99, whereas the control group had a feed to gain ratio of 7.88. That is, a 23.9% improvement in feed efficiency was observed in the experimental group supplemented with the water-soluble formulation of the present disclosure as compared to the control group on the same ration but without the water-soluble formulation of the present disclosure (FIG. 2).

Example 5—Reducing Cost Per Pound of Weight Gain of a Market Animal

The compositions disclosed herein can reduce the cost of raising a market animal. By increasing feed efficiency (lowering the feed to gain ratio), the animal consumes less food, and therefore, costs less to raise. For example, consider the following hypothetical scenario (adapted from beefresearch.ca/topics/optimizing-feedlot-efficiency):two steer calves (A and B) placed on feed gaining an average 3.5 pounds per day. Steer A consumes an average of 21 lbs dry matter per day, which equates to a 6:1 feed to gain ratio. Steer B consumes 28 lb/day, having a feed to gain ratio of 8:1, and therefore is less feed efficient than Steer A. Based on a ration cost of 0.085 cents per pound, Steer A costs $1.79 to feed per day, whereas Steer B costs $2.38 per day. If both steers reach their finish weight in 200 days, the less feed efficient animal (Steer B) would cost the producer $119 more to finish than an animal with better feed efficiency (Steer A). In other words, the animal with the more efficient feed to gain ratio costs about 25% less to raise to market. Additional examples of cumulative cost differences are shown below in Table 6 (adapted from extension.usu.edu/4h-livestock-calculator/research/market-animal-feed-efficiency-a-tool-for-evaluating-feed-conversion).

TABLE 6

Cumulative cost differences

| | Cost per pound of gain | | Cost difference | % Reduction from less |
|---|---|---|---|---|
| Species | More efficient | Less efficient | per 100 lbs | to more efficient |
| Cattle | $2.25 | $3.75 | $170 | 40% |
| Sheep | $2.05 | $5.85 | $280 | 65% |
| Goat | $1.95 | $5.25 | $270 | 63% |
| Hog | $1.30 | $1.75 | $140 | 26% |

Example 6—Reduced Enteric Methane Emissions from Ruminant Animals

The compositions described herein can be administered to ruminant animals, such as cattle, sheep, goats, etc. to reduce enteric methane emissions. In one example, the composition can be used as a feed additive, added directly on top of the food (as a so-called top-dress) or mixed into the total mixed ration (TMR). In another example, the composition can be added directly to the animal's water source. Additional ingredients may be added enhance the flavor, nutrition, and/or shelf life of the composition. The composition may also be incorporated in the manufacture of compounded animal feeds or lick blocks. In another example, the composition can be administered within capsules or other edible containers.

Depending on the ruminant animal, the composition may be administered continuously, every hour, every day, every other day, once a week, etc., in a range from 0.01 mg to 1 mg per kg of the animal's body weight. The composition may be made available in the form of food or water ad libitum.

As the ruminant animal consumes the composition, enteric methane emissions may be reduced from 1% to 100% compared to other ruminant animals not receiving the composition.

Example 7—Compositions of the Disclosure Exhibit Improved Release Profiles

Earlier sections of this disclosure describe the beneficial properties of compositions of the present disclosure for rapid and consistent administration of antimethanogenic compounds to ruminants. Administrations of antimethanogenic compounds in carriers from Table 2 resulted in rapid absorption and effect, as measured by more immediate reduced methane emissions. To test the relative improvement, the effects of the example compositions of Table 3 will be compared against comparable doses of antimethanogenic compounds delivered via and oil carrier. Briefly, test compositions of the present disclosure (e.g., seaweed extract with high bromoform concentration dissolved in propylene glycol), will be administered to a ruminant animal. A control group will be administered same levels of the same antimethanogen as the test composition, in an oil carrier, to a second, comparable ruminant animal. Methane emissions for animals receiving the test and control compositions will be tracked prior to, and after administration of the antimethanogenic compounds.

It is expected that animals receiving the compositions of the present disclosure, in water-soluble carriers will exhibit faster methane reduction responses than control animals receiving comparable oil-based compositions.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

NUMBERED EMBODIMENTS OF THE DISCLOSURE

Notwithstanding the appended claims, the disclosure sets forth the following numbered embodiments:

1. A water-soluble composition comprising:
   a) an antimethanogenic compound; and
   b) a carrier,
   wherein the carrier is miscible and/or soluble with water, and wherein the antimethanogenic compound is miscible and/or soluble with the carrier.

2. A water-soluble composition comprising:
   a) an antimethanogenic compound selected from the group consisting of methyl bromide, methyl chloride, methyl iodide, methyl fluoride, bromodichloromethane, trichlorethylene, bromoform, chloroform, iodoform, fluoroform, dibromomethane, and a combination thereof; and
   b) a carrier selected from Table 2,
   wherein the antimethanogenic compound is dissolved in the carrier, and wherein the carrier is miscible and/or soluble with water.

3. An animal feed composition comprising:
   a) an antimethanogenic compound dissolved in a carrier that is miscible and/or soluble in water; and
   b) an animal nutritional component;
   wherein the animal feed composition reduces enteric methane emissions and/or increases feed efficiency when ingested by a ruminant animal.

4. A composition comprising:
   a) an algae extract; and
   b) a carrier,
   wherein the algae extract comprises an antimethanogenic compound, and wherein the carrier is miscible and/or soluble with water.

5. The composition of any one of embodiments 1-4, wherein the carrier is a non-toxic carrier.

6. The composition of any one of embodiments 1-5, wherein the carrier has an approximate vapor pressure of less than 1 kPa at between 20° C.-25° C.

7. The composition of any one of embodiments 1, 3, and 5-6 wherein the antimethanogenic compound is an enzymatic inhibitor.

7.1 The composition of any one of embodiments 1, 3, and 5-6 wherein the antimethanogenic compound is a microflora modifying inhibitor.

7.2 The composition of any one of embodiments 1, 3, and 5-6 wherein the antimethanogenic compound is a hydrogen receptor.

7.3 The composition of any one of embodiments 1, and 3-6 wherein the antimethanogenic compound is selected from methyl bromide, methyl chloride, methyl iodide, methyl fluoride, bromodichloromethane, trichlorethylene, bromoform, chloroform, iodoform, fluoroform, dibromomethane, and combinations thereof.

7.4 The composition of any one of embodiments 1-7.3, wherein the composition is capable of being absorbed by a ruminant within 1, 2, 3, 4, 5, 6, 7, 8, 9, 10, 11, 12, 13, 14, or 15 hours.

7.5 The composition of embodiment 7.4, wherein absorption is measured by speed and strength of reduced methane emissions.

7.6 The composition of any one of embodiments 1-7.3, wherein the composition exhibits rapid effects when administered to a ruminant animal.

7.7 The composition of claim 7.6, wherein the composition achieves maximum methane reduction faster than a comparable antimethanogenic dose in an oil carrier.

7.8 The composition of claim 7.6, wherein the composition achieves maximum methane reduction within 1, 2, 3, 4, 5, 6, 7, 8, 9, 10, 11, 12, 13, 14, or 15 hours.

8. The composition of any one of embodiments 1-3, or 5-7.8, wherein the antimethanogenic compound is a synthetic.

9. The composition of any one of embodiments 1-3, wherein the antimethanogenic compound is an organism extract.

10. The composition of embodiment 9, wherein the organism is an algae.

11. The composition of any one of embodiments 4-10, wherein the algae is a red algae from order Rhodophyta.

12. The composition of any one of embodiments 4-10, wherein the algae is a red algae from order Bonnemaisoniales.

13. The composition of any one of embodiments 4-10, wherein the algae is a red algae from genus *Asparagopsis*.

14. The composition of any one of embodiments 4-10, wherein the algae comprises algae selected from the group consisting of: algae of class Florideophyceae, algae of genus *Gracilaria*, algae of genus *Palmeria*, and genus *Chondrus*.

15. The composition of any one of embodiments 4-10, wherein the algae comprises brown algae of class Phaeophyceae.

16. The composition of any one of embodiments 4-10, wherein the algae comprises green algae.

17. The composition of any one of embodiments 4-10, wherein the algae comprises an algae selected from the group consisting of *Laminaria, Macrocystis pyrifera* and *Dictyota*.

18. The composition of embodiment 9, wherein the organism is a plant.

19. The composition of embodiment 9, wherein the organism is a fungi.

20. The composition of embodiment 9, wherein the organism is a bacteria.

21. The composition of any one of any one of embodiments 1-20, wherein the carrier is a water-soluble alcohol.

22. The composition of embodiment 21, wherein the water-soluble alcohol is propylene glycol and the antimethanogenic compound is bromoform.

23. The composition of any one of embodiments 1-20, wherein the carrier is a glycol selected from propylene glycol, diethylene glycol, dipropylene glycol, triethylene glycol, and combinations thereof.

24. The composition of any one of embodiments 1-23, wherein the composition comprises a flavoring.

25. The composition of any one of embodiments 1-24, wherein the composition comprises water.

26. The composition of any one of embodiments 1-25, wherein the composition comprises a solid animal feed.

27. The composition of any one of embodiments 1-26, wherein the carrier has an approximate vapor pressure of less than 0.5 kPa.

28. The composition of any one of embodiments 1-26, wherein the carrier has an approximate vapor pressure of less than 100 Pa.

29. The composition of any one of embodiments 1-26, wherein the carrier has an approximate vapor pressure of less than 50 Pa.

30. The composition of any one of embodiments 1-29, wherein the composition further comprises vitamin B12.

31. The composition of any one of embodiments 1-30, where the antimethanogenic compound is at a concentration of at least 0.1 mg/g of carrier.

32. The composition of embodiment 31, where the antimethanogenic compound is at a concentration of at least 0.5 mg/g of carrier.

33. The composition of embodiment 31, where the antimethanogenic compound is at a concentration of at least 1 mg/g of carrier.

34. The composition of embodiment 31, where the antimethanogenic compound is at a concentration of at least 5 mg/g of carrier.
35. The composition of embodiment 31, where the antimethanogenic compound is at a concentration of at least 10 mg/g of carrier.
36. The composition of embodiment 31, where the antimethanogenic compound is at a concentration of at least 15 mg/g of carrier.
37. The composition of embodiment 31, where the antimethanogenic compound is at a concentration of at least 20 mg/g of carrier.
38. The composition of embodiment 31, where the antimethanogenic compound is at a concentration of at least 50 mg/g of carrier.
38.1 The composition of embodiment 31, where the antimethanogenic compound is at a concentration of at least 75 mg/g of carrier.
38.2 The composition of embodiment 31, where the antimethanogenic compound is at a concentration of at least 100 mg/g of carrier.
38.3 The composition of embodiment 31, where the antimethanogenic compound is at a concentration of at least 150 mg/g of carrier.
38.3 The composition of embodiment 31, where the antimethanogenic compound is at a concentration of at least 200 mg/g of carrier.
38.4 The composition of embodiment 31, where the antimethanogenic compound is at a concentration of at least 500 mg/g of carrier. 38.5 The composition of embodiment 31, where the antimethanogenic compound is at a concentration of between 1.0 mg/g of carrier and 100 mg/g of carrier.
38.6 The composition of embodiment 31, where the antimethanogenic compound is at a concentration of between 100 mg/g of carrier and 200 mg/g of carrier.
38.7 The composition of embodiment 31, where the antimethanogenic compound is at a concentration of between 400 mg/g of carrier and 800 mg/g of carrier.
38.8 The composition of any one of embodiments 1-31, wherein the carrier is propylene glycol, the antimethanogenic compound is bromoform, and wherein the bromoform has a concentration of at least 0.1 g/100 mL of propylene glycol.
39. The composition of any one of embodiments 1-31, wherein the carrier is propylene glycol, the antimethanogenic compound is chloroform, and wherein the chloroform has a concentration of at least 0.1 g/100 mL of propylene glycol.
40. The composition of any one of embodiments 1-31, wherein the carrier is propylene glycol, the antimethanogenic compound is iodoform, and wherein the iodoform has a concentration of at least 0.1 g/100 mL of propylene glycol.
41. The composition of any one of embodiments 38-40, wherein the antimethanogenic compound has a concentration of at least 0.5 g/100 mL of propylene glycol.
42. The composition of any one of embodiments 38-40, wherein the antimethanogenic compound has a concentration of at least 1 g/100 mL of propylene glycol.
43. The composition of any one of embodiments 38-40, wherein the antimethanogenic compound has a concentration of at least 5 g/100 mL of propylene glycol.
44. The composition of any one of embodiments 38-40, wherein the antimethanogenic compound has a concentration of at least 10 g/100 mL of propylene glycol.
45. The composition of any one of embodiments 38-40, wherein the antimethanogenic compound has a concentration of at least 15 g/100 mL of propylene glycol.
46. The composition of any one of embodiments 38-40, wherein the antimethanogenic compound has a concentration of at least 20 g/100 mL of propylene glycol.
47. A composition comprising: bromoform dissolved in propylene glycol, wherein the composition comprises at least 0.1 mg of bromoform per gram of propylene glycol.
48. The composition of embodiment 47, wherein the composition comprises at least 0.5 mg of bromoform per gram of propylene glycol.
49. The composition of embodiment 47, wherein the composition comprises at least 1 mg of bromoform per gram of propylene glycol.
50. The composition of embodiment 47, wherein the composition comprises at least 5 mg of bromoform per gram of propylene glycol.
51. The composition of embodiment 47, wherein the composition comprises at least 10 mg of bromoform per gram of propylene glycol.
52. The composition of embodiment 47, wherein the composition comprises at least 15 mg of bromoform per gram of propylene glycol.
53. The composition of embodiment 47, wherein the composition comprises at least 20 mg of bromoform per gram of propylene glycol.
53.1 The composition of embodiment 47, wherein the composition comprises at least 50 mg of bromoform per gram of propylene glycol.
53.2 The composition of embodiment 47, wherein the composition comprises at least 75 mg of bromoform per gram of propylene glycol.
53.3 The composition of embodiment 47, wherein the composition comprises at least 100 mg of bromoform per gram of propylene glycol.
53.4 The composition of embodiment 47, wherein the composition comprises at least 300 mg of bromoform per gram of propylene glycol.
53.5 The composition of embodiment 47, wherein the composition comprises at least 500 mg of bromoform per gram of propylene glycol.
53.6 The composition of embodiment 47, wherein the composition comprises between 300 mg to 700 mg of bromoform per gram of propylene glycol.
53.7 The composition of embodiment 47, wherein the composition comprises at least 100 mg to 1000 mg of bromoform per gram of propylene glycol.
54. A method for increasing feed efficiency in a ruminant animal, the method comprising: administering the composition of any one of embodiments 1-53.7 to a ruminant animal, wherein a ruminant animal receiving the composition exhibits at least a 0.5% increase in feed efficiency compared to a ruminant animal that did not receive the composition.
55. The method of embodiment 54, wherein the ruminant animal receiving the composition exhibits at least a 1% increase in feed efficiency compared to a ruminant animal that did not receive the composition.
56. The method of embodiment 54, wherein the ruminant animal receiving the composition exhibits at least a 5% increase in feed efficiency compared to a ruminant animal that did not receive the composition.
57. The method of embodiment 54, wherein the ruminant animal receiving the composition exhibits at least a 10% increase in feed efficiency compared to a ruminant animal that did not receive the composition.
58. The method of embodiment 54, wherein the ruminant animal receiving the composition exhibits at least a 15% increase in feed efficiency compared to a ruminant animal that did not receive the composition.

59. The method of embodiment 54, wherein the ruminant animal receiving the composition exhibits at least a 20% increase in feed efficiency compared to a ruminant animal that did not receive the composition.

60. The method of embodiment 54, wherein the ruminant animal receiving the composition exhibits at least a 25% increase in feed efficiency compared to a ruminant animal that did not receive the composition.

61. A method for decreasing enteric methane emissions from a ruminant animal, the method comprising administering the composition of any one of embodiments 1-53 to a ruminant animal, wherein a ruminant animal receiving the composition exhibits at least a 10% decrease in enteric methane emissions compared to a ruminant animal that did not receive the composition.

62. The method of embodiment 61, wherein the ruminant animal receiving the composition exhibits at least a 15% decrease in enteric methane emissions compared to a ruminant animal that did not receive the composition.

63. The method of embodiment 61, wherein the ruminant animal receiving the composition exhibits at least a 20% decrease in enteric methane emissions compared to a ruminant animal that did not receive the composition.

64. The method of embodiment 61, wherein the ruminant animal receiving the composition exhibits at least a 25% decrease in enteric methane emissions compared to a ruminant animal that did not receive the composition.

65. The method of embodiment 61, wherein the ruminant animal receiving the composition exhibits at least a 30% decrease in enteric methane emissions compared to a ruminant animal that did not receive the composition.

66. The method of embodiment 61, wherein the ruminant animal receiving the composition exhibits at least a 40% decrease in enteric methane emissions compared to a ruminant animal that did not receive the composition.

67. The method of embodiment 61, wherein the ruminant animal receiving the composition exhibits at least a 50% decrease in enteric methane emissions compared to a ruminant animal that did not receive the composition.

68. A method for delivering an antimethanogenic compound to a ruminant animal, the method comprising: adding the composition of any one of embodiments 1-53 to a ruminant's water supply.

69. The method of embodiment 68, wherein the ruminant exhibits at least a 0.5% increase in feed efficiency and at least a 10% decrease in enteric methane emissions compared to a ruminant without access to the water supply.

70. The method of any one of embodiments 54-69, wherein the ruminant animal is selected from cattle, goat, sheep, and bison.

71. The method of any one of embodiments 54-69, wherein the ruminant animal is a breed of cattle selected from Angus, Ayrshire, Beefmaster, Belgium Blue, Belted Galloway, Brahman, or Zebu, Brangus, British White, Brown Swiss, Charolais, Chianina, Devon, Dexter, English Longhorn, Galloway, Gloucester, Guernsey, Hereford, or Whiteface, Highland, Holstein-Friesian, Irish Moiled, Jersey, Kerry, Limousin, Luing, Milking Devon, Milking Shorthorn, Normande, Polled Hereford, Red Angus, Red Poll, Santa Gertrudis, Shorthorn, or Durham, South Devon, Simmental, Sussex, Welsh Black, and White Park.

72. The method of any one of embodiments 54-71, wherein the composition is administered in a range from 0.01 mg to 1 mg per kg of body weight of the ruminant animal.

73. The method of any one of embodiments 54-71, wherein the composition is administered in a range from 0.1 mg to 1 mg per kg of body weight of the ruminant animal.

74. The method of any one of embodiments 54-73, wherein the composition is administered every day.

75. The method of any one of embodiments 54-73, wherein the composition is administered every 2 days.

76. The method of any one of embodiments 54-73, wherein the composition is administered every 7 days.

77. A method of capturing antimethanogenic compounds, comprising the steps of:
   a) providing a first solution comprising an antimethanogenic compound in a non-water soluble carrier;
   b) providing a second solution comprising a water-soluble carrier selected from Table 2; and
   c) contacting the first solution and second solution, thereby transferring the antimethanogenic compound from the first solution to the second solution.

77.1 A method of capturing antimethanogenic compounds, comprising the steps of:
   a) providing a first solution comprising an antimethanogenic compound in an oil carrier;
   b) providing a second solution comprising a propylene glycol; and
   c) contacting the first solution and second solution, thereby transferring the antimethanogenic compound from the first solution to the second solution.

77.2 A method of capturing antimethanogenic compounds, comprising the steps of:
   a) capturing antimethanogenic compounds from a water solution by contacting the water solution with a non-miscible oil, thereby transferring antimethanogenic compounds to the non-miscible oil;
   b) separating the non-miscible oil from the water, thereby making a first solution; and
   c) contacting the first solution with a second solution comprising a water-soluble carrier selected from Table 2; thereby transferring the antimethanogenic compound from the first solution to the second solution.

77.2.5 A method of capturing antimethanogenic compounds, comprising the steps of:
   a) providing a first solution comprising an antimethanogenic compound in an oil carrier;
   b) providing a second solution comprising a water-soluble carrier; and
   c) contacting the first solution and second solution, thereby transferring the antimethanogenic compound from the first solution to the second solution.

77.3 The method of embodiment 77.2.5, wherein the water-soluble carrier is propylene glycol.

78. The method of any one of embodiments 77-77.3, wherein the contacting the first solution and second solution occurs at a 1:1 ratio.

79. The method of any one of embodiments 77-78, wherein the second solution is able to capture at least 25% of the antimethanogenic compound from the first solution.

80. The method of embodiment 77, wherein the non-water-soluble carrier is oil.

80.1 The method of any one of embodiments 77-80, wherein the antimethanogenic compound selected from the group consisting of methyl bromide, methyl chloride, methyl iodide, methyl fluoride, bromodichloromethane, trichlorethylene, bromoform, chloroform, iodoform, fluoroform, dibromomethane, and a combination thereof.

80.2. The method of any one of embodiments 77-80.2, wherein the contacting includes mixing, stirring, shaking, or the like.

81. A method of capturing antimethanogenic gas, comprising the steps of:
   contacting the antimethanogenic gas with a water-soluble carrier selected from Table 2;
   wherein the antimethanogenic gas is retained within the water-soluble carrier.

81.1 A method of capturing antimethanogenic gas, comprising the steps of:
   contacting the antimethanogenic gas with an oil carrier, wherein the antimethanogenic gas is retained within the oil carrier.

81.2. A method of concentrating antimethanogenic compounds, comprising the steps of:
   contacting the antimethanogenic compound with a water-soluble carrier selected from Table 2 or an oil;
   wherein the antimethanogenic compound reaches a concentration of at least 10, 20, 30, 40, 50, or 60 grams of antimethanogenic compound per milliliter of water-soluble carrier or oil.

81.3 The method of embodiment 81 or 81.1, wherein at least 10%, 20%, 30%, 40%, 50%, 60%, 70%, 80%, or 90% of the antimethanogenic compound in the gas is retained within the liquid carrier.

82. A method of extracting antimethanogenic compounds from a cell, comprising the steps of:
   a) providing a cell containing an antimethanogenic compound;
   b) heating the cell, thereby creating a heated gas above the cell, said heated gas comprising the antimethanogenic compound; and
   c) contacting the heated gas with a liquid carrier;
   wherein antimethanogenic compound in the heated gas is retained within the liquid carrier.

82.1 The method of embodiment 82, wherein at least 10%, 20%, 30%, 40%, 50%, 60%, 70%, 80%, or 90% of the antimethanogenic compound in the gas is retained within the liquid carrier.

83. A method of extracting antimethanogenic compounds from a cell, comprising the steps of:
   a) providing a cell containing an antimethanogenic compound;
   b) off gassing the cell, thereby creating a gas above the cell, said gas comprising the antimethanogenic compound; and
   c) contacting the gas of step (b) with a liquid carrier;
   wherein antimethanogenic compound in the gas is retained within the liquid carrier.

83.1 The method of embodiment 83, wherein at least 10%, 20%, 30%, 40%, 50%, 60%, 70%, 80%, or 90% of the antimethanogenic compound in the gas is retained within the liquid carrier.

84. The method of embodiment 82-83.1, wherein the liquid carrier is an oil.

85. The method of embodiment 82-83.1, wherein the liquid carrier is a water-soluble carrier selected from Table 2.

86. The method of any one of embodiments 81, 81.2 and 85, wherein the water-soluble carrier is a glycol.

87. The method of any one of embodiments 81, 81.2 and 85, wherein the water-soluble carrier is propylene glycol.

88. The method of any one of embodiments 82-87, wherein the cell is an algae cell.

89. The method of any one of embodiments 82-87, wherein the cell is a recombinant microbial cell producing an antimethanogenic compound.

90. The method of any one of embodiments and 88, wherein the algae is selected from the group consisting of *Laminaria saccharina, Laminaria digitata, Fucus vesiculosis, Fuscus distichus, Alaria esculenta, Chorda filum, Ceramium rubrum, Corallina pilulifera, Pelvetia canaliculate, Ascophyllum nodusum, Chondrus crispus, Plocamium hamatum, Gigartina stellata, Enteromorpha linza, Ulva lacta, Bonnemaisonia hamifera, Asparagopsis taxiformis, Asparagopsis Armata, Gracilaria* spp., *Antithamnionella sarniensis, Antithamnion plumula*, and *Macrocystis pyrifera*.

91. The method of any one of embodiments 81-90, wherein the antimethanogenic compound selected from the group consisting of methyl bromide, methyl chloride, methyl iodide, methyl fluoride, bromodichloromethane, trichlorethylene, bromoform, chloroform, iodoform, fluoroform, dibromomethane, and a combination thereof.

92. The method of embodiment 83, wherein the off gassing the cell is enhanced through heating.

93. The method of embodiment 83, wherein the off gassing the cell is enhanced by circulating air around the cell.

94. The method of any one of embodiments 82-93, wherein the resulting antimethanogenic compound that is retained within the carrier contains fewer contaminants compared to a control extract produced by directly contacting the carrier with the cell.

95. The method of any one of embodiments 77-83, wherein the contacting comprises bubbling the gas through the carrier.

What is claimed is:

1. A method of extracting antimethanogenic compounds from a cell, comprising the steps of:
   a) providing a cell containing an antimethanogenic compound;
   b) off-gassing the cell, thereby creating a gas above the cell, said gas comprising the antimethanogenic compound; and
   c) contacting the gas of step (b) with a liquid carrier;
   wherein the antimethanogenic compound in the gas is retained within the liquid carrier.

2. The method of claim 1, wherein the liquid carrier is an oil.

3. The method of claim 1, wherein the liquid carrier is a glycol.

4. The method of claim 1, wherein the liquid carrier is a water-soluble carrier selected from the group consisting of acetic acid, diethylene glycol, dipropylene glycol, propylene glycol, and triethylene glycol.

5. The method of claim 4, wherein the water-soluble carrier is propylene glycol.

6. The method of claim 1, wherein the cell is an algal cell.

7. The method of claim 1, wherein the cell is a recombinant microbial cell producing an antimethanogenic compound.

8. The method of claim 6, wherein the algal cell is selected from the group consisting of *Laminaria saccharina, Laminaria digitata, Fucus vesiculosis, Fucus distichus, Alaria esculenta, Chorda filum, Ceramium rubrum, Corallina pilulifera, Pelvetia canaliculate, Ascophyllum nodusum, Chondrus crispus, Plocamium hamatum, Gigartina stellata, Enteromorpha linza, Ulva lacta, Bonnemaisonia hamifera, Asparagopsis taxiformis, Asparagopsis armata, Gracilaria* spp., *Antithamnionella sarniensis, Antithamnion plumula*, and *Macrocystis pyrifera*.

9. The method of claim 1, wherein the antimethanogenic compound is selected from the group consisting of methyl bromide, methyl chloride, methyl iodide, methyl fluoride, bromodichloromethane, trichlorethylene, bromoform, chloroform, iodoform, fluoroform, dibromomethane, and a combination thereof.

10. The method of claim 1, wherein the off-gassing the cell is enhanced through heating.

11. The method of claim 1, wherein the off-gassing the cell is enhanced by circulating air around the cell.

12. The method of claim 1, wherein the antimethanogenic compound that is retained within the liquid carrier contains fewer non-antimethanogenic compound contaminants compared to a control extract produced by directly contacting the liquid carrier with the cell.

13. The method of claim 1, wherein the contacting of step (c) comprises bubbling the gas through the liquid carrier.

14. The method of claim 1, wherein at least 60% of the antimethanogenic compound in the gas is retained within the liquid carrier.

15. The method of claim 1, wherein the cell is suspended in liquid.

16. The method of claim 1, wherein the liquid carrier is propylene glycol, and the liquid carrier comprises at least 5 mg of the antimethanogenic compound per milliliter of liquid carrier after step (c).

17. The method of claim 1, wherein the liquid carrier is oil, and the liquid carrier comprises at least 0.1 g of the antimethanogenic compound per milliliter of liquid carrier after step (c).

18. The method of claim 2, wherein the oil is an edible oil.

19. The method of claim 2, wherein the oil is selected from the group consisting of canola oil, olive oil, corn oil, mineral oil, soybean oil, corn oil, palm kernel oil, rapeseed oil, sunflower oil, safflower oil, coconut oil, rice bran oil, sesame oil, flaxseed oil, hemp oil, cottonseed oil, peanut oil, almond oil, beech nut oil, brazil nut oil, cashew oil, hazelnut oil, macadamia oil, mongongo nut oil, pecan oil, pine nut oil, pistachio oil, walnut oil, pumpkin seed oil, grapefruit seed oil, lemon oil, apricot oil, apple seed oil, argan oil, avocado oil, orange oil, and combinations thereof.

20. A method of producing a bromoform-rich liquid solution, comprising the steps of:
 a) providing an algae cell containing bromoform;
 b) off-gassing the algae cell, thereby creating a gas above the algae cell, said gas comprising the bromoform; and
 c) contacting the gas of step (b) with a liquid carrier; thereby producing a bromoform-rich liquid solution; wherein the liquid carrier is a glycol.

* * * * *